US012752044B2

(12) United States Patent
Kelleher et al.

(10) Patent No.: US 12,752,044 B2
(45) Date of Patent: Oct. 6, 2026

(54) OXYGENATOR WITH IMPROVED BLOOD MIXING

(71) Applicant: CardiacAssist, Inc., Pittsburgh, PA (US)

(72) Inventors: Kelli Kelleher, Glenshaw, PA (US); Ruben Hartogs, Pittsburgh, PA (US); Luke Simpson, Pittsburgh, PA (US); Robert Svitek, Freeport, PA (US)

(73) Assignee: CardiacAssist, Inc.

( * ) Notice: Subject to any disclaimer, the term of this patent is extended or adjusted under 35 U.S.C. 154(b) by 609 days.

(21) Appl. No.: 18/204,776

(22) Filed: Jun. 1, 2023

(65) Prior Publication Data

US 2024/0399037 A1 Dec. 5, 2024

(51) Int. Cl.
*A61M 1/16* (2006.01)

(52) U.S. Cl.
CPC ........ *A61M 1/1625* (2014.02); *A61M 1/1698* (2013.01)

(58) Field of Classification Search
CPC .... A61M 1/1698; A61M 1/267; A61M 1/262; A61M 1/1623; A61M 1/1621; A61M 1/26; A61M 1/265
See application file for complete search history.

(56) References Cited

U.S. PATENT DOCUMENTS 4,376,095 A * 3/1983 Hasegawa ............ B01D 63/022 422/46
4,791,054 A * 12/1988 Hamada ............... B01D 63/031 422/46
5,501,663 A * 3/1996 Hattler ................ A61M 1/1678 261/DIG. 28
(Continued)

FOREIGN PATENT DOCUMENTS

DE 102005023152 A1 6/2006
EP 1833529 B1 2/2013
(Continued)

OTHER PUBLICATIONS

Affinity Fusion™ Oxygenation System, Medtronic, 10 pages.
(Continued)

*Primary Examiner* — Philip R Wiest
*Assistant Examiner* — Meagan Ngo
(74) *Attorney, Agent, or Firm* — Seager, Tufte & Wickhem LLP

(57) ABSTRACT

An oxygenator may include a housing extending from a first end to a second end along a central longitudinal axis, a first end cap, a second end cap, and a bundle of hollow gas exchange fibers extending between the first end and the second end. The first end cap and the second end cap may each be rotatable about the central longitudinal axis. An oxygenator may include a bundle of hollow gas exchange fibers extending from the first end cap to the second end cap. An oxygenator may include a housing including a first axially expandable portion, a second axially expandable portion, and a rigid tubular portion disposed between and fixedly attached to the first and second axially expandable portions. An oxygenator may include a bundle of hollow gas exchange fibers may be axially movable relative to the housing.

18 Claims, 9 Drawing Sheets

(56) References Cited

U.S. PATENT DOCUMENTS

| | | | | |
|---|---|---|---|---|
| 5,626,759 | A * | 5/1997 | Krantz ................ | A61M 1/1698 422/46 |
| 8,318,092 | B2 | 11/2012 | Reggiani et al. | |
| 8,388,566 | B2 | 3/2013 | Reggiani et al. | |
| 8,394,049 | B2 | 3/2013 | Reggiani et al. | |
| 8,647,569 | B1 | 2/2014 | Federspiel et al. | |
| 8,652,406 | B2 | 2/2014 | Reggiani et al. | |
| 8,795,220 | B2 | 8/2014 | Reggiani et al. | |
| 8,980,176 | B2 | 3/2015 | Reggiani et al. | |
| 9,162,022 | B2 | 10/2015 | Reggiani et al. | |
| 9,402,943 | B2 | 8/2016 | Reggiani et al. | |
| 10,098,994 | B2 | 10/2018 | Silvestri et al. | |
| 10,159,777 | B2 | 12/2018 | Reggiani et al. | |
| 10,335,530 | B2 | 7/2019 | Madhani et al. | |
| 10,369,262 | B2 | 8/2019 | Reggiani | |
| 10,549,022 | B2 | 2/2020 | Jeffries et al. | |
| 10,661,004 | B2 | 5/2020 | Mazzoli et al. | |
| 11,160,912 | B2 | 11/2021 | Reggiani et al. | |
| 11,471,577 | B2 | 10/2022 | Reggiano | |
| 2002/0143397 | A1* | 10/2002 | von Segesser ...... | A61M 1/1698 128/205.28 |
| 2004/0052681 | A1* | 3/2004 | Mortensen .......... | A61M 1/1625 604/6.14 |
| 2005/0232811 | A1* | 10/2005 | Autschbach ........ | A61M 1/1678 604/6.14 |
| 2014/0065016 | A1 | 3/2014 | Federspiel et al. | |
| 2017/0100531 | A1 | 4/2017 | Madhani et al. | |
| 2020/0237994 | A1 | 7/2020 | Tommasi | |
| 2020/0276377 | A1 | 9/2020 | Mazzoli et al. | |
| 2021/0077701 | A1 | 3/2021 | Silvestri et al. | |
| 2022/0168483 | A1 | 6/2022 | Zaniboni et al. | |
| 2022/0184287 | A1 | 6/2022 | Gesler et al. | |
| 2022/0211925 | A1 | 7/2022 | Gesler et al. | |
| 2022/0409797 | A1 | 12/2022 | Zaniboni | |
| 2023/0001063 | A1 | 1/2023 | Reggiano | |

FOREIGN PATENT DOCUMENTS

| | | | |
|---|---|---|---|
| WO | 02078768 | A2 | 10/2002 |
| WO | 2012066439 | A1 | 5/2012 |
| WO | 2012156907 | A1 | 11/2012 |
| WO | 2021076437 | A1 | 4/2021 |
| WO | 2021191661 | A1 | 9/2021 |

OTHER PUBLICATIONS

Capiox® FX Advance, Oxygenator with Integrated Arterial Filter and Hardshell Reservoir, Terumo Vascular, 12 pages, 2020.

Inspire@ Oxygenator Family, LivaNova Cardiopulmonary, 11 pages, 2022.

Nautilis ™ Ecmo Oxygenator Quick Reference Guide, Medtronic, 2 pages, 2020.

Paragon Adult Maxi PMP Oxygenator, Chalice Medical Limited, 4 pages, Feb. 19, 2018.

Verbelen et al., “First In Vivo Assessment of RAS-Q Technology as Lung Support Device for Pulmonary Hypertension,” The International Journal of Artificial Organs, vol. 44, No. 4, pp. 243-250, 2020.

* cited by examiner

OXYGENATOR WITH IMPROVED BLOOD MIXING

TECHNICAL FIELD

The present disclosure relates generally to extracorporeal circulation. More particularly, the present disclosure relates to extracorporeal blood conditioning devices and methods for conditioning blood in extracorporeal circulation.

BACKGROUND

Generally, hollow fiber blood oxygenators that are used to exchange oxygen (O2) and carbon dioxide (CO2) in extracorporeal circulation have one of two forms. Either the oxygenator has a cylindrical housing with a crisscross hollow fiber mat spirally wound around a cylindrical central core, or the oxygenator has a polygonal housing with stacked (piled) hollow fiber mat layers. Blood flows outside the hollow fiber lumens and oxygenating gases flow inside the hollow fiber lumens.

In cylindrically wound oxygenators, blood flow across the hollow fibers may be radial, longitudinal, circumferential, or a combination of two or more of these. In some cases, this may lead to a blood flow path that is relatively long and non-laminar to guarantee high gas exchange efficiency with reduced surface area and limited device priming volume, which are important parameters for optimal patient perfusion.

In some oxygenators, blood stagnation may occur in isolated areas where low (or lower) blood flow occurs. Blood tends to follow the path of least resistance through the oxygenator, while a uniform flow and/or resistance is desirable. Locations where blood flow is reduced may stagnate, resulting in thrombus formation. Alternative oxygenator configurations which may disrupt the blood flow path and/or enhance mixing of blood within the oxygenator may result in reduced stagnation, reduced thrombus formation, and/or improved oxygenation.

There is an ongoing need for alternative devices, components, and/or methods of use and/or manufacture of said devices and/or components.

SUMMARY

In one example, an oxygenator may comprise a housing extending from a first end to a second end along a central longitudinal axis, a first end cap fixedly attached to the first end of the housing, a second end cap fixedly attached to the second end of the housing, and a bundle of hollow gas exchange fibers extending between the first end of the housing and the second end of the housing. The first end cap and the second end cap may each be rotatable about the central longitudinal axis.

In addition or alternatively to any example disclosed herein, the housing includes a flexible portion disposed between the first end and the second end.

In addition or alternatively to any example disclosed herein, the housing extends continuously from the first end of the housing to the second end of the housing.

In addition or alternatively to any example disclosed herein, the bundle of hollow gas exchange fibers comprises a first bundle of hollow gas exchange fibers extending between the first end of the housing and a middle junction disposed between the first end of the housing and the second end of the housing, and a second bundle of hollow gas exchange fibers extending between the middle junction and the second end of the housing.

In addition or alternatively to any example disclosed herein, the first end cap is rotatable about the central longitudinal axis in a first direction and the second end cap is rotatable about the central longitudinal axis in a second direction opposite the first direction simultaneously with the first end cap.

In addition or alternatively to any example disclosed herein, the first bundle of hollow gas exchange fibers and the second bundle of hollow gas exchange fibers are each fixedly attached to the middle junction.

In addition or alternatively to any example disclosed herein, rotation of the first end cap and the second end cap about the central longitudinal axis in opposite directions moves the first end cap closer to the second end cap.

In addition or alternatively to any example disclosed herein, the first end cap and the second end cap are each configured to oscillate between the first direction and the second direction.

In addition or alternatively to any example disclosed herein, the housing includes a first housing portion fixedly attached to the first end cap and a second housing portion fixedly attached to the second end cap, wherein the first housing portion is axially spaced apart from the second housing portion.

In addition or alternatively to any example disclosed herein, the first housing portion is rotatable relative to the second housing portion.

In addition or alternatively to any example disclosed herein, the first housing portion is coupled to the second housing portion by a bridge section.

In addition or alternatively to any example disclosed herein, the first housing portion is rotatable relative to the bridge section and the second housing portion is rotatable relative to the bridge section.

In addition or alternatively to any example disclosed herein, the first housing portion comprises a first bundle of hollow gas exchange fibers and the second housing portion comprises a second bundle of hollow gas exchange fibers.

In addition or alternatively to any example disclosed herein, an oxygenator may comprise a housing extending from a first end to a second end along a central longitudinal axis, a first end cap fixedly attached to the first end of the housing, a second end cap fixedly attached to the second end of the housing, and a bundle of hollow gas exchange fibers extending from the first end cap to the second end cap. The housing may comprise a first accordion portion fixedly attached to the first end cap, a second accordion portion fixedly attached to the second end cap, and a rigid tubular portion disposed between and fixedly attached to the first accordion portion and the second accordion portion.

In addition or alternatively to any example disclosed herein, the first end cap is a fixed distance from the second end cap.

In addition or alternatively to any example disclosed herein, the rigid tubular portion is axially movable along the central longitudinal axis relative to the first end cap and the second end cap.

In addition or alternatively to any example disclosed herein, the oxygenator may further comprise an actuation apparatus configured to translate the rigid tubular portion axially along the central longitudinal axis.

In addition or alternatively to any example disclosed herein, the actuation mechanism is configured to oscillate the rigid tubular portion axially back and forth along the central longitudinal axis.

In addition or alternatively to any example disclosed herein, an oxygenator may comprise a housing extending from a first end to a second end along a central longitudinal axis, a first end cap fixedly attached to the first end of the housing, a second end cap fixedly attached to the second end of the housing, and a bundle of hollow gas exchange fibers extending between the first end cap and the second end. The bundle of hollow gas exchange fibers may be axially movable relative to the housing along the central longitudinal axis.

In addition or alternatively to any example disclosed herein, the oxygenator may further comprise a first accordion portion fixedly attached to the first end cap and defining a first accordion chamber between the bundle of hollow gas exchange fibers and the first end cap, and a second accordion portion fixedly attached to the second end cap and defining a second accordion chamber spaced apart from the first accordion chamber between the bundle of hollow gas exchange fibers and the second end cap.

In addition or alternatively to any example disclosed herein, the housing has a fixed axial length.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

and

Figure 9:
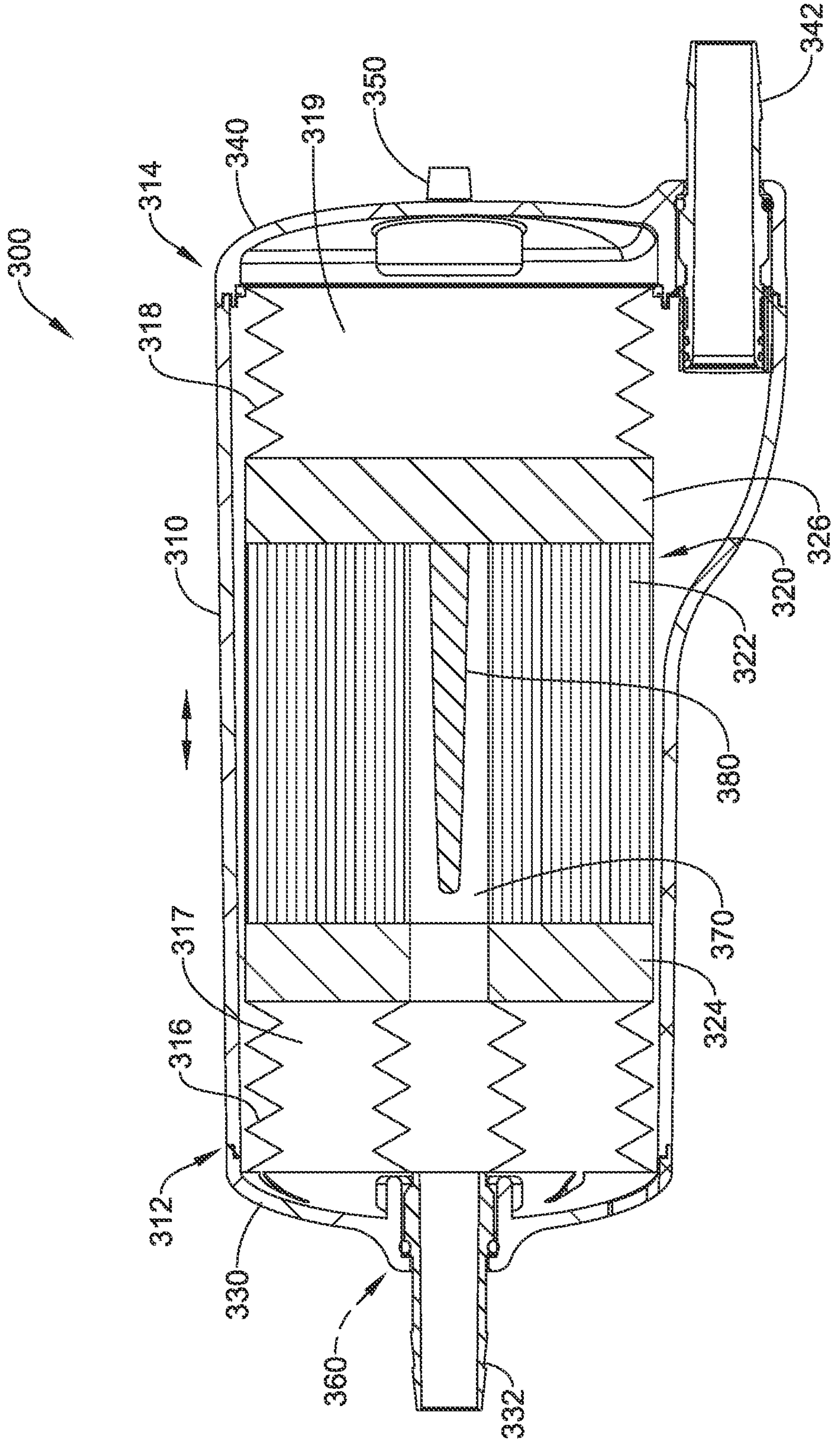

FIG. 9 illustrates an oxygenator including an axially movable gas exchanger disposed within a housing.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate example embodiments of the disclosure but not limit the disclosure. Those skilled in the art will recognize that the various elements described and/or shown may be arranged in various combinations and configurations without departing from the scope of the disclosure. However, in the interest of clarity and ease of understanding, every feature and/or element may not be shown in each drawing.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently-such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to some features may be equally referred to all instances and quantities beyond one of said feature(s) unless clearly stated to the contrary. As such, it will be understood that the following discussion may apply equally to any and/or all of the components for which there are more than one within the device, etc. unless explicitly stated to the contrary.

Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

FIGS. 1-4 illustrate selected aspects of an oxygenator 100 for conditioning blood in extracorporeal circulation, such as with an extracorporeal life support (ECLS) system, for example. In some embodiments, the oxygenator 100 may comprise a housing 110 extending from a first end 112 to a second end 114 opposite the first end 112. In some embodiments, the housing 110 or portions thereof may be rigid and/or may be constructed from a substantially rigid material. In some embodiments, the housing 110 or portions thereof may be semi-rigid and/or may be constructed from a semi-rigid material. In some embodiments, the housing 110 or portions thereof may be flexible and/or may be constructed from a flexible material. In some embodiments, the housing 110 may be elongated in shape, with a central longitudinal axis extending from the first end 112 to the second end 114. In some embodiments, at least a portion of the housing 110 extending along the central longitudinal axis may be substantially cylindrical in shape.

The oxygenator 100 and/or the housing 110 may include a first cover or a first end cap 130 coupled to the first end 112 of the housing 110. In some embodiments, the first cover or the first end cap 130 may be fixedly attached to the housing 110. In some embodiments, the first cover or the first end cap 130 may be fixedly attached at the first end 112 of the housing 110. In some embodiments, the first cover or the first end cap 130 may be integrally and/or monolithically formed with the housing 110 as a single structure. In some alternative embodiments, the first cover or the first end cap 130 may be removable from the housing 110. Other configurations are also contemplated.

The oxygenator 100 and/or the housing 110 may include a second cover or a second end cap 140 coupled to the second end 114 of the housing 110. In some embodiments, the second cover or the second end cap 140 may be fixedly attached to the housing 110. In some embodiments, the second cover or the second end cap 140 may be fixedly attached at the second end 114 of the housing 110. In some embodiments, the second cover or the second end cap 140 may be integrally and/or monolithically formed with the housing 110 as a single structure. In some alternative embodiments, the second cover or the second end cap 140 may be removable from the housing 110. Other configurations are also contemplated.

The oxygenator 100 may comprise a gas exchanger 120 disposed within the housing 110. In some embodiments, the gas exchanger 120 may be disposed between the first end 112 of the housing 110 and the second end 114 of the housing 110. In at least some embodiments, the gas exchanger 120 may include a bundle of hollow gas exchange fibers 122. In some embodiments, the bundle of hollow gas exchange fibers 122 may extend between the first end 112 of the housing 110 and the second end 114 of the housing 110. In some embodiments, the bundle of hollow gas exchange fibers 122 may extend from the first end 112 of the housing

110 to the second end 114 of the housing 110. Other configurations are also contemplated.

In some embodiments, the gas exchanger 120 may include a first potting body 124 disposed proximate the first end 112 of the housing 110 and a second potting body 126 disposed proximate the second end 114 of the housing 110. The bundle of hollow gas exchange fibers 122 may extend from the first potting body 124 to the second potting body 126. In some embodiments, the first potting body 124 and/or the second potting body 126 may be formed from resin or a polymeric material. Proximal and/or upstream ends of the bundle of hollow gas exchange fibers 122 may be fixedly attached to and/or may be embedded within the first potting body 124. Distal and/or downstream ends of the bundle of hollow gas exchange fibers 122 may be fixedly attached to and/or may be embedded within the second potting body 126. The gas exchanger 120 may be configured such that blood flow through the gas exchanger 120 may pass over and/or around the bundle of hollow gas exchange fibers 122 to facilitate gas exchange therebetween.

The first cover or the first end cap 130 and the second cover or the second end cap 140 may be disposed on opposite sides of the gas exchanger 120 and/or the bundle of hollow gas exchange fibers 122. The oxygenator 100, the housing 110, and/or the first cover or the first end cap 130 may include a blood inlet port 132 in fluid communication with the gas exchanger 120 and configured to connect to an extracorporeal life support system. The blood inlet port 132 may be configured to be in fluid communication with a patient's venous blood flow. In some embodiments, the blood inlet port 132 may be disposed and/or positioned upstream of the gas exchanger 120. In some embodiments, the blood inlet port 132 may be disposed proximate the first end 112 of the housing 110. In some embodiments, the housing 110 and/or the first cover or the first end cap 130 may include a purging line port through which air can be purged from the oxygenator 100 and/or the housing 110.

The oxygenator 100, the housing 110, and/or the second cover or the second end cap 140 may include a blood outlet port 142 in fluid communication with the gas exchanger 120 and configured to connect to the extracorporeal life support system. The blood outlet port 142 may be configured to be in fluid communication with a patient's arterial blood flow. In some embodiments, the blood outlet port 142 may be disposed and/or positioned downstream of the gas exchanger 120. In some embodiments, the blood outlet port 142 may be disposed proximate the second end 114 of the housing 110. In at least some embodiments, the blood outlet port 142 may be disposed on an opposite side of the gas exchanger 120 and/or the bundle of hollow gas exchange fibers 122 from the blood inlet port 132.

Figure 2:
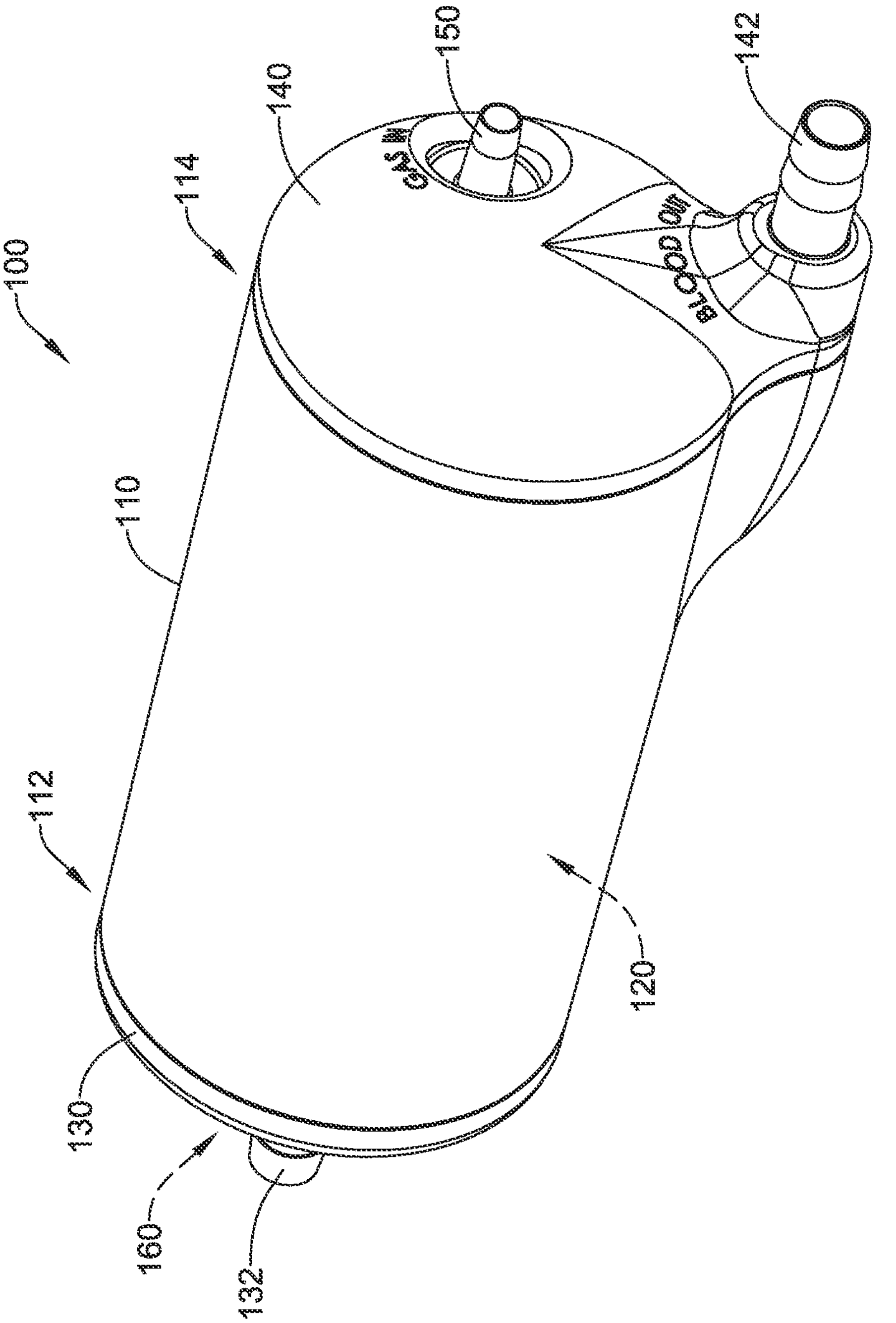
FIG. 2 is a right perspective view illustrating selected aspects of the oxygenator of FIG. 1.
Figure 3:
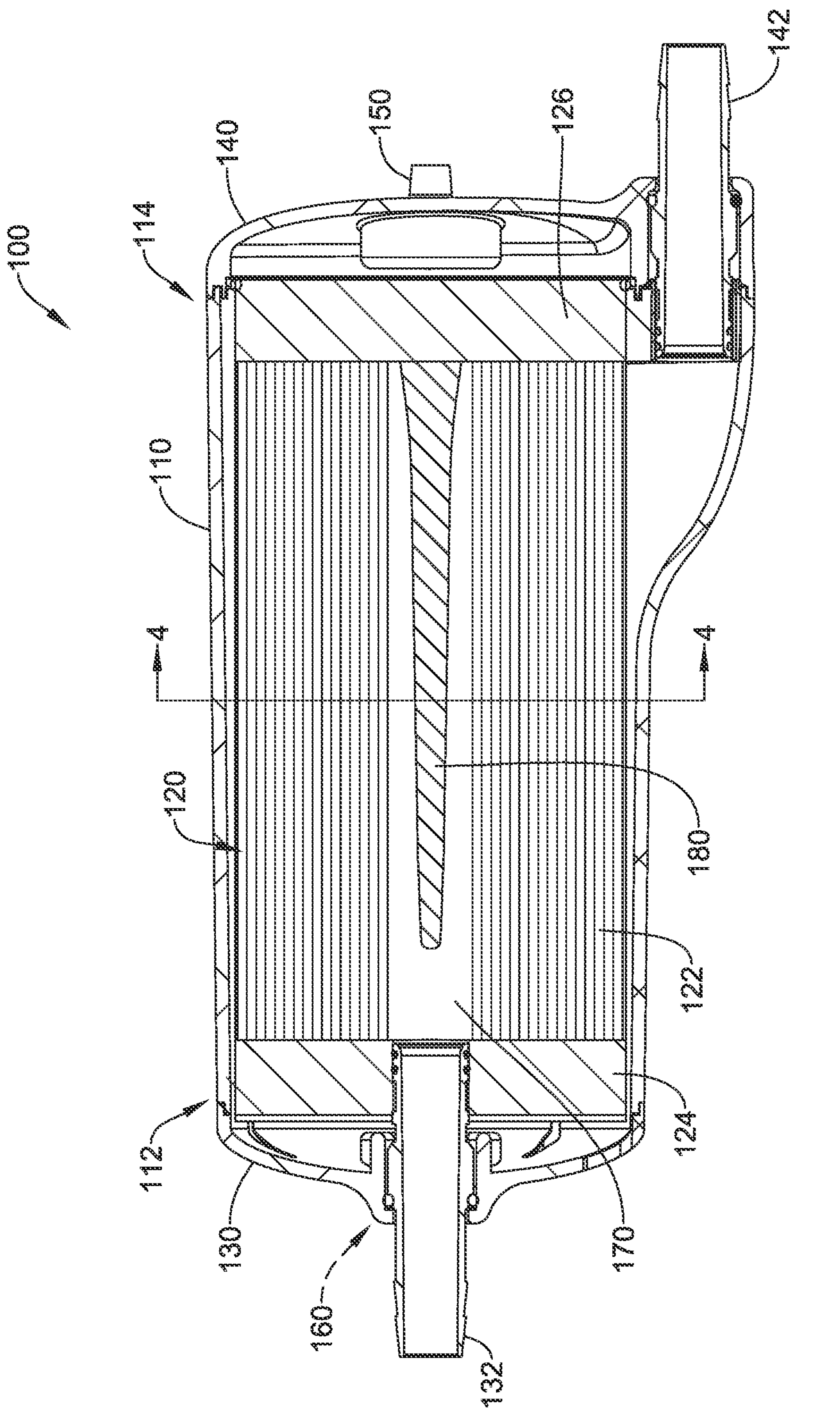
FIG. 3 is a partial cross-sectional view illustrating selected aspects of the oxygenator of FIGS. 1-2.
Figure 4:
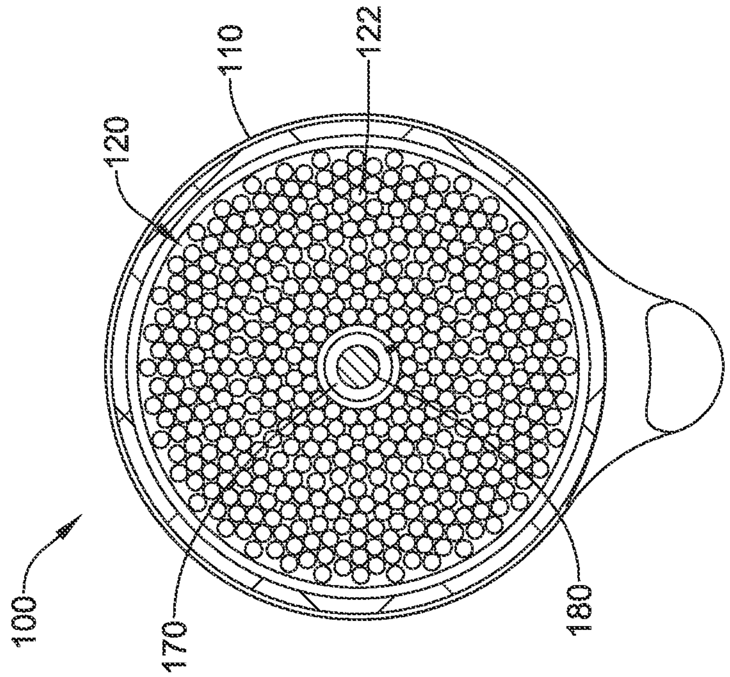
FIG. 4 is a transverse cross-sectional view of the oxygenator of FIGS. 1-2 taken along the line 4-4 of FIG. 3.

The oxygenator 100 and/or the housing 110 may include a gas inlet port 150 in fluid communication with the gas exchanger 120, the first potting body 124, and/or the bundle of hollow gas exchange fibers 122. In some embodiments, the gas inlet port 150 may be disposed in and/or adjacent to the second cover or the second end cap 140, as seen in FIG. 2. In some embodiments, the gas inlet port 150 may be disposed at a position that is laterally and/or radially offset from the central longitudinal axis of the housing 110. In some embodiments, the gas inlet port 150 may be disposed at a position that is coaxial with the central longitudinal axis of the housing 110. Other configurations are also contemplated. The gas inlet port 150 may be configured to connect to a gas supply source via tubing (not shown) to transport gas (e.g., oxygen, air, etc.) to the oxygenator 100, the gas exchanger 120, and/or the bundle of hollow gas exchange fibers 122.

Figure 1:
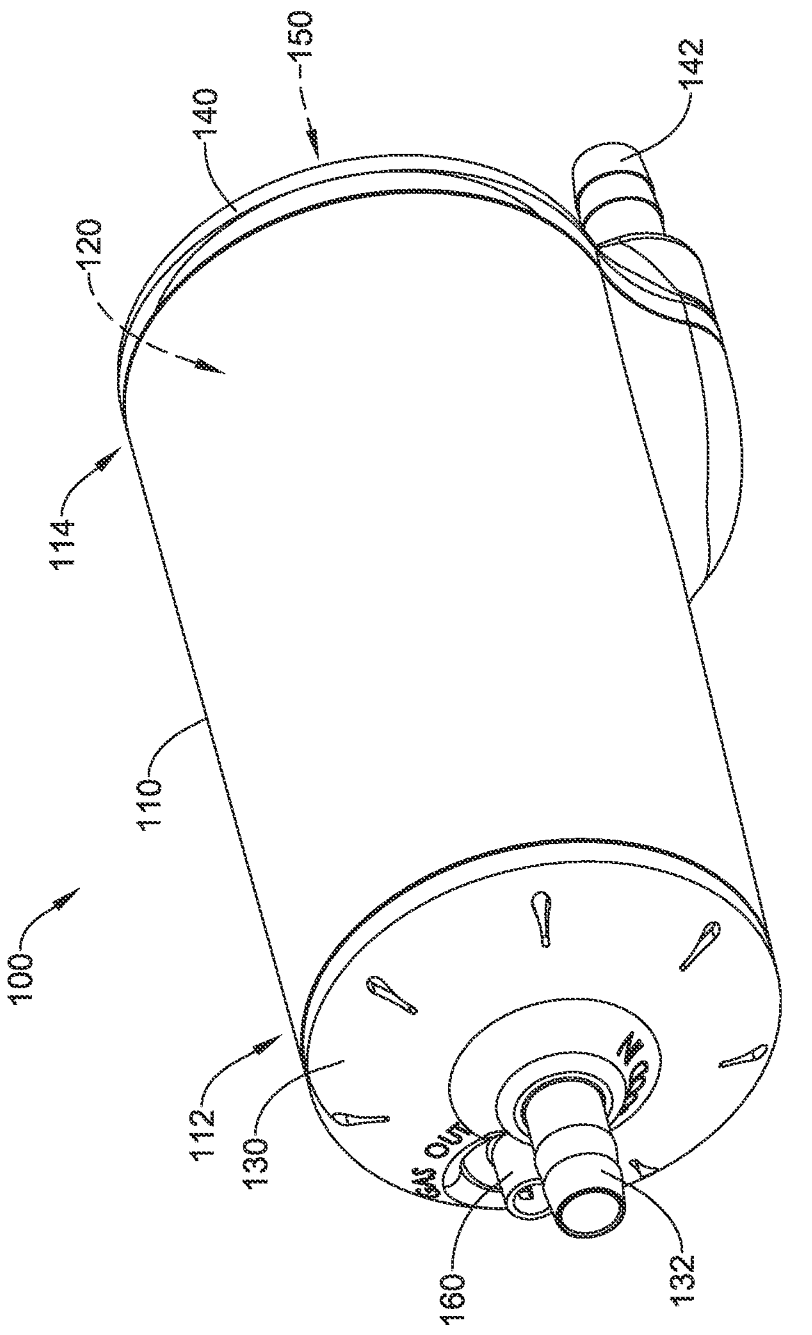
FIG. 1 is a left perspective view illustrating selected aspects of an oxygenator.

The oxygenator 100 and/or the housing 110 may include a gas outlet port 160 in fluid communication with the gas exchanger 120, the second potting body 126, and/or the bundle of hollow gas exchange fibers 122. In some embodiments, the gas outlet port 160 may be disposed in and/or adjacent to the first cover or the first end cap 130, as seen in FIG. 1. In some embodiments, the gas outlet port 160 may be disposed at a position that is laterally and/or radially offset from the central longitudinal axis of the housing 110. In some embodiments, the gas outlet port 160 may be disposed at a position that is coaxial with the central longitudinal axis of the housing 110. Other configurations are also contemplated. The gas outlet port 160 may be configured to transport gas (e.g., oxygen, carbon dioxide, air, etc.) away from the oxygenator 100. In some embodiments, the gas outlet port 160 may be in fluid communication with the atmosphere. In some alternative embodiments, the gas outlet port 160 may be configured to connect to a vacuum source, such as via tubing. In some embodiments, the oxygenator 100 and/or the housing 110 may be devoid of a dedicated gas outlet port in fluid communication with the gas exchanger 120, the second potting body 126, and/or the bundle of hollow gas exchange fibers 122. In some embodiments, the oxygenator 100 and/or the housing 110 may include one or more vent openings disposed in and/or adjacent to the first cover or the first end cap 130 and in fluid communication with the gas exchanger 120, the second potting body 126, and/or the bundle of hollow gas exchange fibers 122. In some embodiments, the oxygenator 100 and/or the housing 110 may include the gas outlet port 160 and the one or more vent openings disposed in and/or adjacent to the first cover or the first end cap 130. In some embodiments, the one or more vent openings may be vented to atmosphere.

In some embodiments, the bundle of hollow gas exchange fibers 122 may be disposed within the housing 110. In some embodiments, the bundle of hollow gas exchange fibers 122 may extend between the first end 112 of the housing 110 and the second end 114 of the housing 110. In some embodiments, the bundle of hollow gas exchange fibers 122 may extend longitudinally between the first end 112 of the housing 110 and the second end 114 of the housing 110. In some embodiments, the bundle of hollow gas exchange fibers 122 may extend from the first end 112 of the housing 110 to the second end of the housing 110. As discussed herein, the bundle of hollow gas exchange fibers 122 may extend from the first potting body 124 to the second potting body 126.

The bundle of hollow gas exchange fibers 122 may be arranged in one or more configurations. In some embodiments, the bundle of hollow gas exchange fibers 122 may be arranged such that the bundle of hollow gas exchange fibers 122 is substantially parallel to each other and/or the central longitudinal axis of the housing 110. In some embodiments, the bundle of hollow gas exchange fibers 122 may be arranged such that the bundle of hollow gas exchange fibers 122 is wound around the central longitudinal axis of the housing 110. In some embodiments, the bundle of hollow gas exchange fibers 122 may be arranged such that the bundle of hollow gas exchange fibers 122 is wound around the central longitudinal axis of the housing 110. In some embodiments, the bundle of hollow gas exchange fibers 122 may be arranged such that the bundle of hollow gas exchange fibers 122 is wound helically around the central longitudinal axis of the housing 110. In some embodiments, the bundle of hollow gas exchange fibers 122 may be arranged in a plurality of layers, wherein fibers within each layer are oriented at an oblique angle to fibers within each immediately adjacent layer. In some embodiments, the bundle of hollow gas exchange fibers 122 may be arranged in a plurality of layers, wherein fibers within each layer are oriented substantially perpendicular to fibers within each immediately adjacent layer. Other configurations, including combinations thereof, are also contemplated.

In some embodiments, the oxygenator 100, the housing 110, and/or the gas exchanger 120 may include a blood lumen 170 disposed therein. The blood lumen 170 may be in fluid communication with the blood inlet port 132 and the blood outlet port 142. In at least some embodiments, the blood lumen 170 may be disposed and/or oriented coaxially with the blood inlet port 132. In at least some embodiments, the blood outlet port 142 may be disposed laterally and/or radially offset from the blood lumen 170. The blood lumen 170 may carry and/or direct blood flowing into the oxygenator 100 and/or the housing 110 into and/or through the gas exchanger 120.

In some embodiments, the oxygenator 100, the housing 110, and/or the gas exchanger 120 may include a diverter 180 disposed therein. In some embodiments, the diverter 180 may be disposed along and/or parallel to the central longitudinal axis of the housing 110. In some embodiments, the diverter 180 may be disposed in line with and/or coaxial with the blood inlet port 132. In some embodiments, the diverter 180 may be disposed within the blood lumen 170 and/or the gas exchanger 120. The diverter 180 may be configured to disrupt blood flow within the blood lumen 170 and/or to direct blood flowing into the gas exchanger 120 radially outward toward and/or into the bundle of hollow gas exchange fibers 122. In some embodiments, the diverter 180 may extend proximally from the second potting body 126. In some embodiments, the diverter 180 may be tapered radially inward in a proximal direction or an upstream direction and/or may be tapered radially outward in a distal direction or a downstream direction. Other configurations are also contemplated. The diverter 180 may be shaped, sized, and configured to limit damage to blood cells (e.g., lysing) as much as possible. In some embodiments, the diverter 180 may include channels, grooves, ridges, guides, blades, etc. formed in or extending from a generally conical outer surface.

During use, gas may be transferred between the gas exchanger 120 and/or the bundle of hollow gas exchange fibers 122 and blood flowing through the oxygenator 100 and/or the gas exchanger 120 (e.g., oxygen into the blood, carbon dioxide out of the blood, etc.).

In some embodiments, a blood conditioning system and/or the oxygenator 100 may include a pump (not shown) configured to drive fluid flow through the oxygenator 100. In some embodiments, the pump may be fluidly coupled to the oxygenator 100 via tubing. In some embodiments, the pump may extend from the housing 110 and/or the first cover or the first end cap 130 of the oxygenator 100. In some embodiments, the pump may be fixedly attached directly to the oxygenator 100, the housing 110, and/or the first cover or the first end cap 130. In some embodiments, the pump may be integrally formed with the housing 110 and/or the first cover or the first end cap 130 of the oxygenator 100. In some embodiments, the blood conditioning system and/or the oxygenator 100 may be devoid of tubing between and/or connecting the pump and the oxygenator 100. Other configurations are also contemplated.

In some embodiments, the blood conditioning system and/or the oxygenator 100 may include a heat exchanger (not shown) configured to exchange heat with the blood. In some embodiments, the oxygenator 100 and the heat exchanger may be disposed within a single, integrated housing. In some embodiments, the heat exchanger may be a standalone device fluidly coupled to the blood conditioning system and/or the oxygenator 100 via tubing. Other configurations are also contemplated.

In some embodiments, the blood conditioning system and/or the oxygenator 100 may include a gaseous microemboli (GME) removal device configured to remove gaseous micro-emboli from the blood. In some embodiments, the oxygenator 100 and the gaseous micro-emboli (GME) removal device may be disposed within a single, integrated housing. In some embodiments, the gaseous micro-emboli (GME) removal device may be a standalone device fluidly coupled to the blood conditioning system and/or the oxygenator 100 via tubing. Other configurations are also contemplated.

While not expressly illustrated, it is also contemplated that the oxygenator 100 may include a cardioplegia port and/or a recirculation port. In some embodiments, the cardioplegia port and/or the recirculation port may be formed in the housing 110. In some embodiments, the cardioplegia port and/or the recirculation port may be formed in and/or may be in fluid communication with the housing 110 and/or an interior thereof. Other configurations and/or features known in the art are also contemplated.

Figure 5:
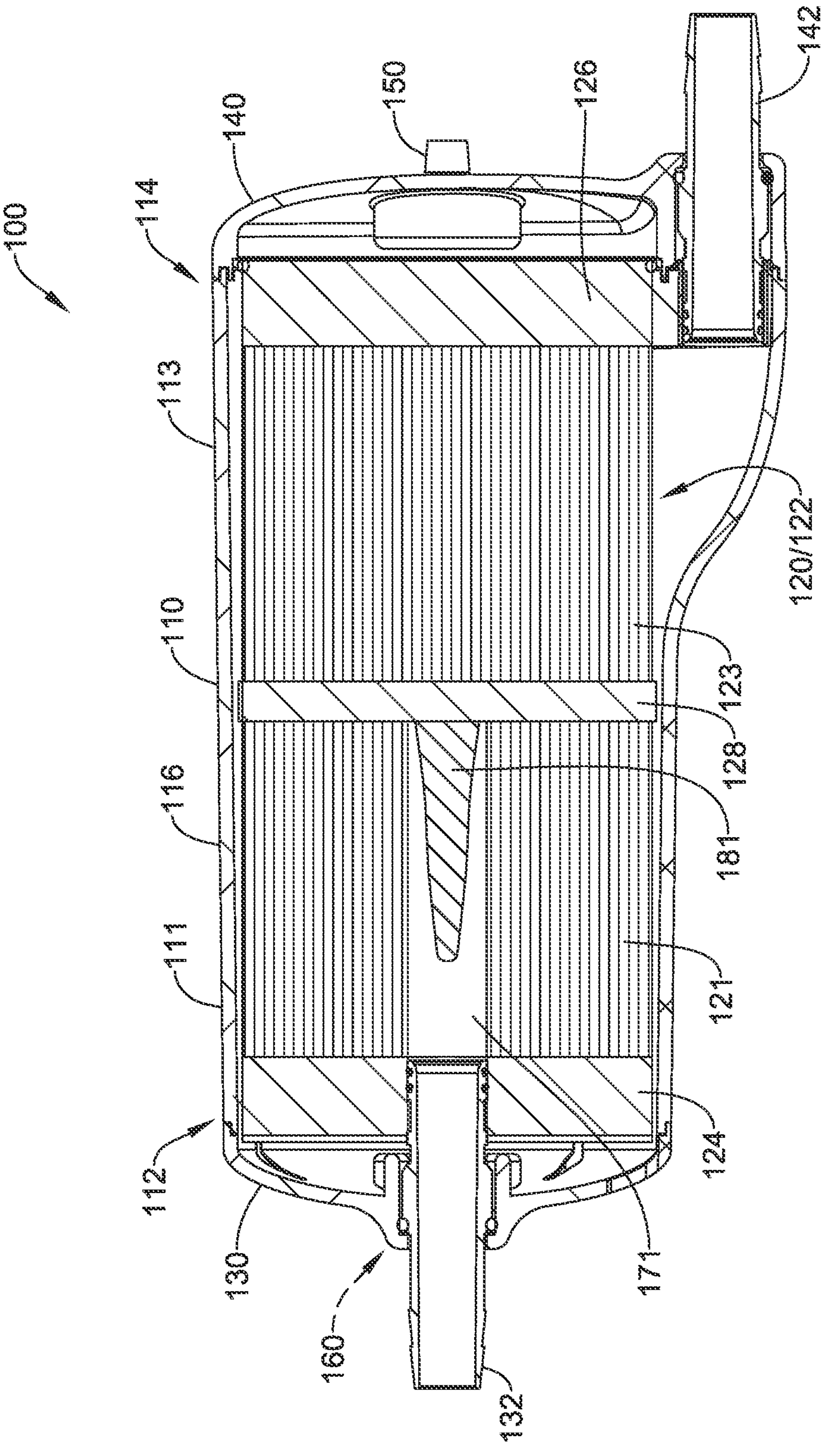
FIGS. 5-6 illustrate an oxygenator including rotatable end caps.
Figure 6:
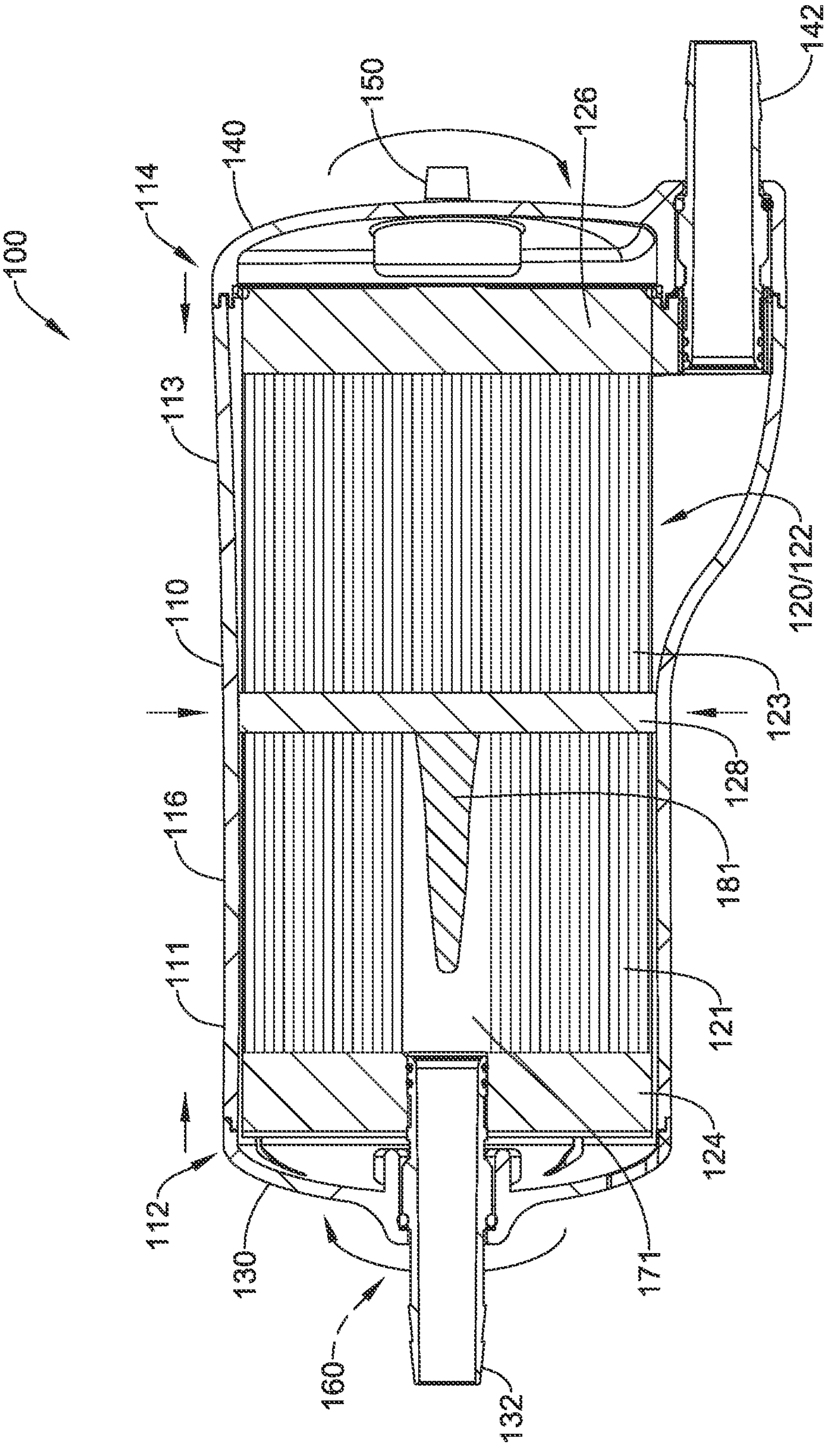

Turning now to FIGS. 5-6, the oxygenator 100 may include a flexible portion 116 disposed between the first end 112 of the housing 110 and the second end 114 of the housing 110. The flexible portion 116 may permit some degree of movement and/or twisting of the housing about and/or around the gas exchanger 120 and/or the bundle of hollow gas exchange fibers 122, as explained herein. In at least some embodiments, the housing 110 may extend continuously from the first end 112 of the housing 110 to the second end 114 of the housing 110.

In some embodiments, the first potting body 124 may be attached and/or secured to the first cover or the first end cap 130. In some embodiments, the first potting body 124 may be fixedly attached to the first cover or the first end cap 130. In some embodiments, the second potting body 126 may be attached and/or secured to the second cover or the second end cap 140. In some embodiments, the second potting body 126 may be fixedly attached to the second cover or the second end cap 140.

In some embodiments, the gas exchanger 120 may include a middle junction 128 disposed proximate a medial portion of the housing 110, and the gas exchanger 120 and/or the bundle of hollow gas exchange fibers 122 may include a first bundle of hollow gas exchange fibers 121 and a second bundle of hollow gas exchange fibers 123. In at least some embodiments, the middle junction 128 may be a third potting body.

The first bundle of hollow gas exchange fibers 121 may extend between the first end 112 of the housing 110 and the middle junction 128 and/or the third potting body. In some embodiments, the first bundle of hollow gas exchange fibers 121 may extend between the first potting body 124 and the middle junction 128 and/or the third potting body. In some embodiments, the first bundle of hollow gas exchange fibers 121 may extend from the first potting body 124 to the middle junction 128 and/or the third potting body.

The second bundle of hollow gas exchange fibers 123 may extend between the middle junction 128 and/or the third potting body and the second end 114 of the housing 110. In some embodiments, the second bundle of hollow gas exchange fibers 123 may extend between the middle junction 128 and/or the third potting body and the second potting body 126. In some embodiments, the second bundle of hollow gas exchange fibers 123 may extend from the middle junction 128 and/or the third potting body to the second potting body 126.

In some embodiments, the middle junction 128 and/or the third potting body may be formed from resin or a polymeric material. In some embodiments, proximal and/or upstream ends of the first bundle of hollow gas exchange fibers 121 may be fixedly attached to and/or may be embedded within the first potting body 124 and distal and/or downstream ends of the first bundle of hollow gas exchange fibers 121 may be fixedly attached to and/or may be embedded within the middle junction 128 and/or the third potting body. In some embodiments, proximal and/or upstream ends of the second bundle of hollow gas exchange fibers 123 may be fixedly attached to and/or may be embedded within the middle junction 128 and/or the third potting body and distal and/or downstream ends of the second bundle of hollow gas exchange fibers 123 may be fixedly attached to and/or may be embedded within the second potting body 126. The gas exchanger 120 may be configured such that blood flow through the gas exchanger 120 may pass over and/or around the first bundle of hollow gas exchange fibers 121 and the second bundle of hollow gas exchange fibers 123 to facilitate gas exchange therebetween.

In some embodiments, the oxygenator 100, the housing 110, and/or the gas exchanger 120 may include a blood lumen 171 disposed therein. The blood lumen 171 may be in fluid communication with the blood inlet port 132 and the blood outlet port 142. In at least some embodiments, the blood lumen 171 may be disposed and/or oriented coaxially with the blood inlet port 132. In at least some embodiments, the blood outlet port 142 may be disposed laterally and/or radially offset from the blood lumen 171. The blood lumen 171 may carry and/or direct blood flowing into the oxygenator 100 and/or the housing 110 into and/or through the gas exchanger 120. In some embodiments, the blood lumen 171 may be disposed within, may extend within, and/or may extend through the first bundle of hollow gas exchange fibers 121.

In some embodiments, the oxygenator 100 and/or the gas exchanger 120 may include a diverter 181 disposed therein. In some embodiments, the diverter 181 may be disposed along and/or parallel to the central longitudinal axis of the housing 110. In some embodiments, the diverter 181 may be disposed in line with and/or coaxial with the blood inlet port 132. In some embodiments, the diverter 181 may be disposed within the blood lumen 171 and/or the gas exchanger 120. The diverter 181 may be configured to disrupt blood flow within the blood lumen 171 and/or to direct blood flowing into the gas exchanger 120 radially outward toward and/or into the first bundle of hollow gas exchange fibers 121. In some embodiments, the diverter 181 may extend proximally from the middle junction 128 and/or the third potting body. In some embodiments, the diverter 181 may be tapered radially inward in a proximal direction or an upstream direction and/or may be tapered radially outward in a distal direction or a downstream direction. Other configurations are also contemplated. The diverter 181 may be shaped, sized, and configured to limit damage to blood cells (e.g., lysing) as much as possible. In some embodiments, the diverter 181 may include channels, grooves, ridges, guides, blades, etc. formed in or extending from a generally conical outer surface.

In some embodiments, the first cover or the first end cap 130 and the second cover or the second end cap 140 are each rotatable about the central longitudinal axis and/or with respect to the gas exchanger 120, the first bundle of hollow gas exchange fibers 121, the second bundle of hollow gas exchange fibers 123, and/or the middle junction 128 and/or the third potting body. In some embodiments, the first cover or the first end cap 130 may be rotatable about the central longitudinal axis in a first direction and the second cover or the second end cap 140 may be rotatable about the central longitudinal axis in a second direction opposite the first direction simultaneously with the first cover or the first end cap 130, thereby twisting the housing 110 about and/or around the gas exchanger 120 and/or the bundle of hollow gas exchange fibers 122, the first bundle of hollow gas exchange fibers 121, the second bundle of hollow gas exchange fibers 123, and/or the middle junction 128 and/or the third potting body.

When the first cover or the first end cap 130 is rotated about the central longitudinal axis in the first direction and the second cover or the second end cap 140 is rotated about the central longitudinal axis in the second direction opposite the first direction simultaneously with the first cover or the first end cap 130, the housing 110 may shorten slightly and/or the medical portion of the housing 110 may radially contract slightly, as seen in FIG. 6. In some embodiments, rotation of the first cover or the first end cap 130 and the second cover or the second end cap 140 about the central longitudinal axis in opposite directions may move the first cover or the first end cap 130 closer to the second cover or the second end cap 140. This movement of the housing 110 and/or the flexible portion 116 of the housing 110 relative to the gas exchanger 120 and/or the bundle of hollow gas exchange fibers 122, the first bundle of hollow gas exchange fibers 121, the second bundle of hollow gas exchange fibers 123, and/or the middle junction 128 and/or the third potting body may cause and/or promote mixing of blood therein and/or may reduce stagnation of blood therein.

In some embodiments, the oxygenator 100 and/or the housing 110 may be configured for manual movement of the housing 110 and/or the flexible portion 116 of the housing 110 relative to the gas exchanger 120 and/or the bundle of hollow gas exchange fibers 122, the first bundle of hollow gas exchange fibers 121, the second bundle of hollow gas exchange fibers 123, and/or the middle junction 128 and/or the third potting body. In some embodiments, the oxygenator 100 and/or the housing 110 may further include an actuation apparatus configured to move the housing 110 and/or the flexible portion 116 of the housing 110 relative to the gas exchanger 120 and/or the bundle of hollow gas exchange fibers 122, the first bundle of hollow gas exchange fibers 121, the second bundle of hollow gas exchange fibers 123, and/or the middle junction 128 and/or the third potting body. In some embodiments, the oxygenator 100 and/or the housing 110 may be configured to move the housing 110 and/or the flexible portion 116 of the housing 110 relative to the gas exchanger 120 and/or the bundle of hollow gas exchange fibers 122, the first bundle of hollow gas exchange fibers 121, the second bundle of hollow gas exchange fibers 123, and/or the middle junction 128 and/or the third potting body in a cyclical manner. In some embodiments, the oxygenator 100 and/or the housing 110 may be configured to move the housing 110 and/or the flexible portion 116 of the housing 110 relative to the gas exchanger 120 and/or the bundle of hollow gas exchange fibers 122, the first bundle of hollow gas exchange fibers 121, the second bundle of hollow gas exchange fibers 123, and/or the middle junction 128 and/or the third potting body in a variable manner. Other configurations are also contemplated.

In some embodiments, the first cover or the first end cap 130 and the second cover or the second end cap 140 are each configured to oscillate between the first direction and the second direction. In some embodiments, oscillation between the first direction and the second direction may be manual. In some embodiments, oscillation between the first direction and the second direction may be automatic. In some embodiments, after moving the first cover or the first end cap 130 in the first direction and the second cover or the second end cap 140 in the second direction opposite the first direction simultaneously with the first cover or the first end cap 130, or vice versa, the first cover or the first end cap 130 and the second cover or the second end cap 140 may be configured to automatically return to an initial position or configuration (e.g., an unbiased configuration).

Figure 7:
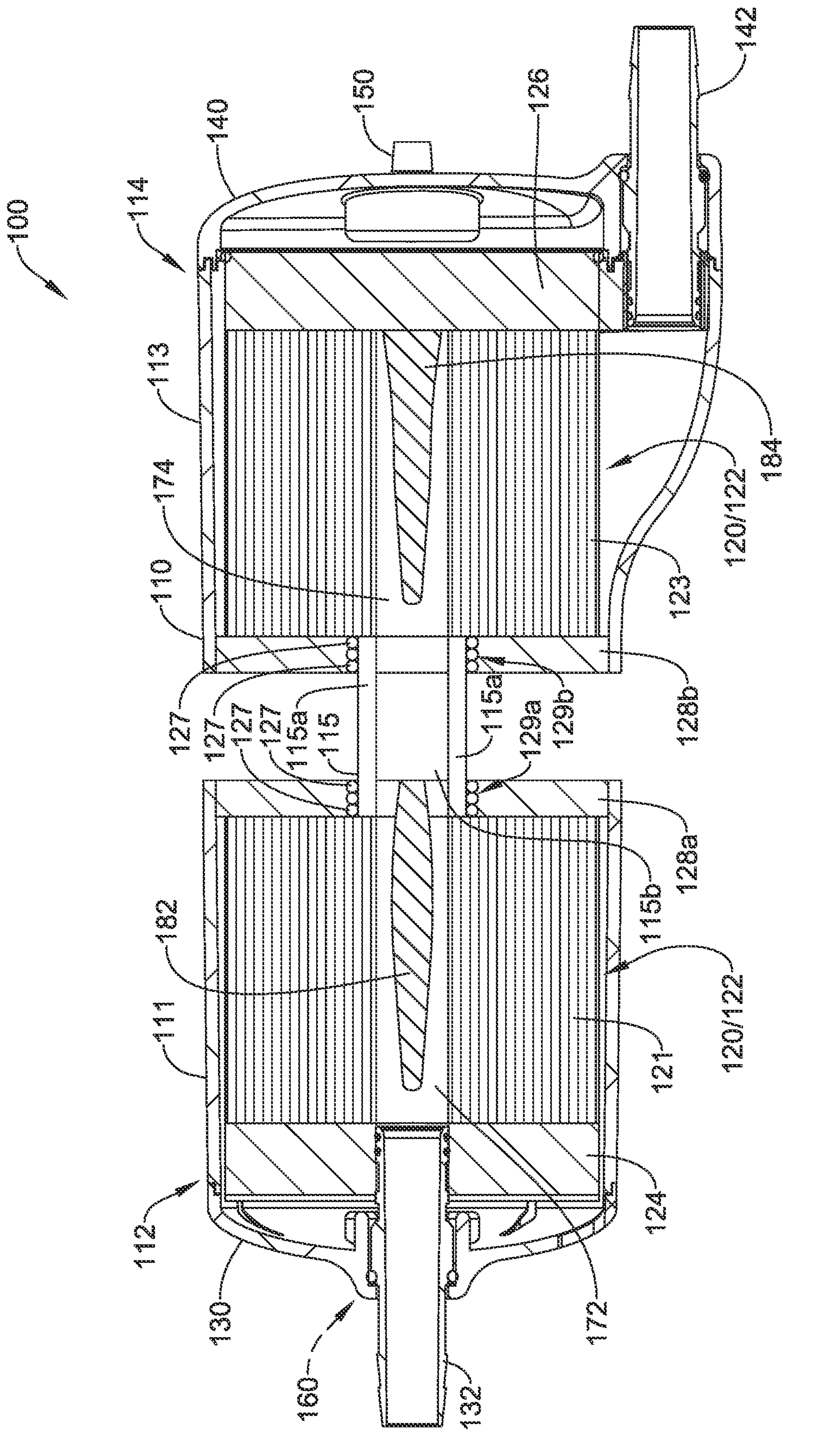
FIG. 7 illustrates an oxygenator including rotatable proximal and distal portions spaced apart from each other.

In some embodiments, the housing 110 may include a first housing portion 111 fixedly attached to the first cover or the first end cap 130 and a second housing portion 113 fixedly attached to the second cover or the second end cap 140. In some embodiments, the first housing portion 111 may be spaced apart from the second housing portion 113. In at least some embodiments, the first housing portion 111 may be axially spaced apart from the second housing portion 113, as seen in FIG. 7. In some embodiments, the first housing portion 111 and/or the first cover or the first end cap 130 may be rotatable about the central longitudinal axis relative to the second housing portion 113 and/or the second cover or the second end cap 140. In at least some embodiments, the first housing portion 111 and/or the second housing portion 113 may be substantially rigid and/or may be formed from a substantially rigid material.

In some embodiments, the first housing portion 111 may be coupled to the second housing portion 113 by a bridge section 115. In some embodiments, the bridge section 115 may have a first outer diameter, the first housing portion 111 may have a second outer diameter, and the second housing portion 113 may have a third outer diameter. In at least some embodiments, the first outer diameter may be less than the second outer diameter and/or the first outer diameter may be less than the third outer diameter. In some embodiments, the second outer diameter may be different from the third outer diameter. In some embodiments, second outer diameter and/or the third outer diameter may be substantially equal. In at least some embodiments, the bridge section 115 may space the first housing portion 111 apart from the second housing portion 113. In some embodiments, the bridge section 115 and/or the gas exchanger 120 may include at least one lumen extending axially through the bridge section 115 from the first housing portion 111 to the second housing portion 113.

In some embodiments, the first housing portion 111 may be rotatable relative to the bridge section 115. In some embodiments, the second housing portion 113 may be rotatable relative to the bridge section 115. In some embodiments, the first housing portion 111 may be rotatable relative to the bridge section 115 and the second housing portion 113 may be rotatable relative to the bridge section 115. In some embodiments, the first housing portion 111 may be rotatable relative to the bridge section 115 and the second housing portion 113 may be rotatable relative to the bridge section 115 simultaneously. In some embodiments, the first housing portion 111 may be rotatable relative to the bridge section 115 and the second housing portion 113 may be rotatable relative to the bridge section 115 simultaneously in opposite rotational directions. Other configurations are also contemplated.

In some embodiments, the first housing portion 111 may be rotatable relative to the bridge section 115 and/or the second housing portion 113, and/or the second housing portion 113 may be rotatable relative to the bridge section 115 and/or the first housing portion 111 without changing an axial length of the housing 110. In some embodiments, the first housing portion 111 may be rotatable relative to the bridge section 115 and/or the second housing portion 113, and/or the second housing portion 113 may be rotatable relative to the bridge section 115 and/or the first housing portion 111 without changing an axial length of the first housing portion 111. In some embodiments, the first housing portion 111 may be rotatable relative to the bridge section 115 and/or the second housing portion 113, and/or the second housing portion 113 may be rotatable relative to the bridge section 115 and/or the first housing portion 111 without changing an axial length of the second housing portion 113. In some embodiments, the first cover or the first end cap 130 may be a fixed axial distance from the second cover or the second end cap 140.

In some embodiments, the housing 110 and/or the gas exchanger 120 may comprise a proximal potting body 128A and a distal potting body 128B. The proximal potting body 128A may be fixedly attached to the first housing portion 111. The distal potting body 128B may be fixedly attached to the second housing portion 113. In some embodiments, the proximal potting body 128A may form a distal wall of the first housing portion 111. In some embodiments, the proximal potting body 128A may be disposed within an interior of the first housing portion 111 adjacent a distal wall of the first housing portion 111. In some embodiments, the distal potting body 128B may form a proximal wall of the second housing portion 113. In some embodiments, the distal potting body 128B may be disposed within an interior of the second housing portion 113 adjacent a proximal wall of the second housing portion 113. Other configurations are also contemplated.

The proximal potting body 128A and/or the distal wall of the first housing portion 111 may be configured to rotatably engage the bridge section 115. In some embodiments, the first housing portion 111, the proximal potting body 128A, and/or the distal wall of the first housing portion 111 may include a first bearing 129A configured to permit rotation of the first housing portion 111, the proximal potting body 128A, and/or the distal wall of the first housing portion 111 relative to a proximal end of the bridge section 115. In some embodiments, the first housing portion 111, the proximal potting body 128A, and/or the distal wall of the first housing portion 111 may include one or more scaling elements 127 (e.g., O-rings, gaskets, etc.) disposed adjacent to and/or engaged with the first bearing 129A, the proximal end of the bridge section 115, etc.

The distal potting body 128B and/or the proximal wall of the second housing portion 113 may be configured to rotatably engage the bridge section 115. In some embodiments, the second housing portion 113, the distal potting body 128B, and/or the proximal wall of the second housing portion 113 may include a second bearing 129B configured to permit rotation of the second housing portion 113, the distal potting body 128B, and/or the proximal wall of the second housing portion 113 relative to a distal end of the bridge section 115. In some embodiments, the second housing portion 113, the distal potting body 128B, and/or the proximal wall of the second housing portion 113 may include one or more sealing elements 127 (e.g., O-rings, gaskets, etc.) disposed adjacent to and/or engaged with the second bearing 129B, the distal end of the bridge section 115, etc. Other configurations are also contemplated.

In some embodiments, the first housing portion 111 may comprise a first bundle of hollow gas exchange fibers 121 disposed therein. In some embodiments, the first housing portion 111 may be rotatable relative to the first bundle of hollow gas exchange fibers 121. In some embodiments, proximal and/or upstream ends of the first bundle of hollow gas exchange fibers 121 may be fixedly attached to and/or may be embedded within the first potting body 124 and distal and/or downstream ends of the first bundle of hollow gas exchange fibers 121 may be fixedly attached to and/or may be embedded within the proximal potting body 128A.

In some embodiments, the second housing portion 113 may comprise a second bundle of hollow gas exchange fibers 123 disposed therein. In some embodiments, the second housing portion 113 may be rotatable relative to the second bundle of hollow gas exchange fibers 123. In some embodiments, proximal and/or upstream ends of the second bundle of hollow gas exchange fibers 123 may be fixedly attached to and/or may be embedded within the distal potting body 128B and distal and/or downstream ends of the second bundle of hollow gas exchange fibers 123 may be fixedly attached to and/or may be embedded within the second potting body 126.

In some embodiments, the first bundle of hollow gas exchange fibers 121 may be fixedly attached to the second bundle of hollow gas exchange fibers 123 by the bridge section 115. Other configurations are also contemplated. In some embodiments, the bridge section 115 may include a gas lumen 115A fluidly coupled to the proximal potting body 128A, the first bundle of hollow gas exchange fibers 121, the distal potting body 128B, and/or the second bundle of hollow gas exchange fibers 123. In some embodiments, the gas lumen 115A may be configured to carry a gas between the first bundle of hollow gas exchange fibers 121 and the second bundle of hollow gas exchange fibers 123. In some embodiments, the bridge section 115 and/or the gas lumen 115A may comprise a plurality of gas lumens fluidly coupled to the proximal potting body 128A, the first bundle of hollow gas exchange fibers 121, the distal potting body 128B, and/or the second bundle of hollow gas exchange fibers 123.

The first housing portion 111 may include a first blood lumen 172 in fluid communication with the blood inlet port 132. The first housing portion 111 may include a first diverter 182 disposed along and/or parallel to the central longitudinal axis of the housing 110. In some embodiments, the first diverter 182 may be disposed in line with and/or coaxial with the blood inlet port 132 and/or the bridge section 115. In some embodiments, the first diverter 182 may be disposed within the first blood lumen 172, the gas exchanger 120, and/or the first bundle of hollow gas exchange fibers 121. The first diverter 182 may be configured to disrupt blood flow within the first blood lumen 172 and/or to direct blood flowing into the gas exchanger 120 radially outward toward and/or into the first bundle of hollow gas exchange fibers 121. In some embodiments, the first diverter 182 may extend proximally from the proximal potting body 128A. In some embodiments, a proximal portion of the first diverter 182 may be tapered radially inward in a proximal direction or an upstream direction from a maximum radial extent of the first diverter 182. A distal portion of the first diverter 182 may be tapered radially inward in a distal direction or a downstream direction from the maximum radial extent of the first diverter 182. The distal portion of the first diverter 182 may be configured to direct blood flow into the bridge section 115. Other configurations are also contemplated. The first diverter 182 may be shaped, sized, and configured to limit damage to blood cells (e.g., lysing) as much as possible. In some embodiments, the first diverter 182 may include channels, grooves, ridges, guides, blades, etc. formed in or extending from an outer surface thereof.

The second housing portion 113 may include a second blood lumen 174 in fluid communication with the bridge section 115, the first blood lumen 172, and/or the blood inlet port 132. The second housing portion 113 may include a second diverter 184 disposed along and/or parallel to the central longitudinal axis of the housing 110. In some embodiments, the second diverter 184 may be disposed in line with and/or coaxial with the blood inlet port 132 and/or the bridge section 115. In some embodiments, the second diverter 184 may be disposed within the second blood lumen 174, the gas exchanger 120, and/or the second bundle of hollow gas exchange fibers 123. The second diverter 184 may be configured to disrupt blood flow within the second blood lumen 174 and/or to direct blood flowing into the gas exchanger 120 radially outward toward and/or into the second bundle of hollow gas exchange fibers 123. In some embodiments, the second diverter 184 may extend proximally from the second potting body 126. In some embodiments, the second diverter 184 may be tapered radially inward in a proximal direction or an upstream direction and/or may be tapered radially outward in a distal direction or a downstream direction. Other configurations are also contemplated. The second diverter 184 may be shaped, sized, and configured to limit damage to blood cells (e.g., lysing) as much as possible. In some embodiments, the second diverter 184 may include channels, grooves, ridges, guides, blades, etc. formed in or extending from a generally conical outer surface.

In some embodiments, the bridge section 115 may include a bridge blood lumen 115B fluidly coupled to the first blood lumen 172 and/or the second blood lumen 174. In some embodiments, the bridge section 115 and/or the bridge blood lumen 115B may comprise a plurality of bridge blood lumens. In some embodiments, the bridge blood lumen 115B may be configured to carry blood from the first housing portion 111 and/or the first blood lumen 172 to the second housing portion 113 and/or the second blood lumen 174.

Rotating the first housing portion 111 and/or the second housing portion 113 relative to the bridge section 115, the gas exchanger 120, the bundle of hollow gas exchange fibers 122, the first bundle of hollow gas exchange fibers 121, and/or the second bundle of hollow gas exchange fibers 123 may cause and/or promote mixing of blood therein and/or may reduce stagnation of blood therein.

In some embodiments, the oxygenator 100 and/or the housing 110 may be configured for manual movement of the first housing portion 111 relative to the gas exchanger 120 and/or the bundle of hollow gas exchange fibers 122, the first bundle of hollow gas exchange fibers 121, and/or the bridge section 115. In some embodiments, the oxygenator 100 and/or the housing 110 may further include a first actuation apparatus configured to move the first housing portion 111 relative to the gas exchanger 120 and/or the bundle of hollow gas exchange fibers 122, the first bundle of hollow gas exchange fibers 121, and/or the bridge section 115. In some embodiments, the oxygenator 100 and/or the housing 110 may be configured to move the first housing portion 111 relative to the gas exchanger 120 and/or the bundle of hollow gas exchange fibers 122, the first bundle of hollow gas exchange fibers 121, and/or the bridge section 115 in a cyclical manner. In some embodiments, the oxygenator 100 and/or the housing 110 may be configured to move the first housing portion 111 relative to the gas exchanger 120 and/or the bundle of hollow gas exchange fibers 122, the first bundle of hollow gas exchange fibers 121, and/or the bridge section 115 in a variable manner. Other configurations are also contemplated.

In some embodiments, the oxygenator 100 and/or the housing 110 may be configured for manual movement of the second housing portion 113 relative to the gas exchanger 120 and/or the bundle of hollow gas exchange fibers 122, the second bundle of hollow gas exchange fibers 123, and/or the bridge section 115. In some embodiments, the oxygenator 100 and/or the housing 110 may further include a second actuation apparatus configured to move the second housing portion 113 relative to the gas exchanger 120 and/or the bundle of hollow gas exchange fibers 122, the second bundle of hollow gas exchange fibers 123, and/or the bridge section 115. In some embodiments, the oxygenator 100 and/or the housing 110 may be configured to move the second housing portion 113 relative to the gas exchanger 120 and/or the bundle of hollow gas exchange fibers 122, the second bundle of hollow gas exchange fibers 123, and/or the bridge section 115 in a cyclical manner. In some embodiments, the oxygenator 100 and/or the housing 110 may be configured to move the second housing portion 113 relative to the gas exchanger 120 and/or the bundle of hollow gas exchange fibers 122, the second bundle of hollow gas exchange fibers 123, and/or the bridge section 115 in a variable manner. Other configurations are also contemplated.

In some embodiments, the first cover or the first housing portion 111 and the second housing portion 113 are each configured to oscillate between the first direction and the second direction. In some embodiments, oscillation between the first direction and the second direction may be manual. In some embodiments, oscillation between the first direction and the second direction may be automatic. In some embodiments, after moving the first housing portion 111 in the first direction and the second housing portion 113 in the second direction opposite the first direction simultaneously with the first housing portion 111, or vice versa, the first housing portion 111 and the second housing portion 113 may be configured to automatically return to an initial position or configuration (e.g., an unbiased configuration).

Figure 8:
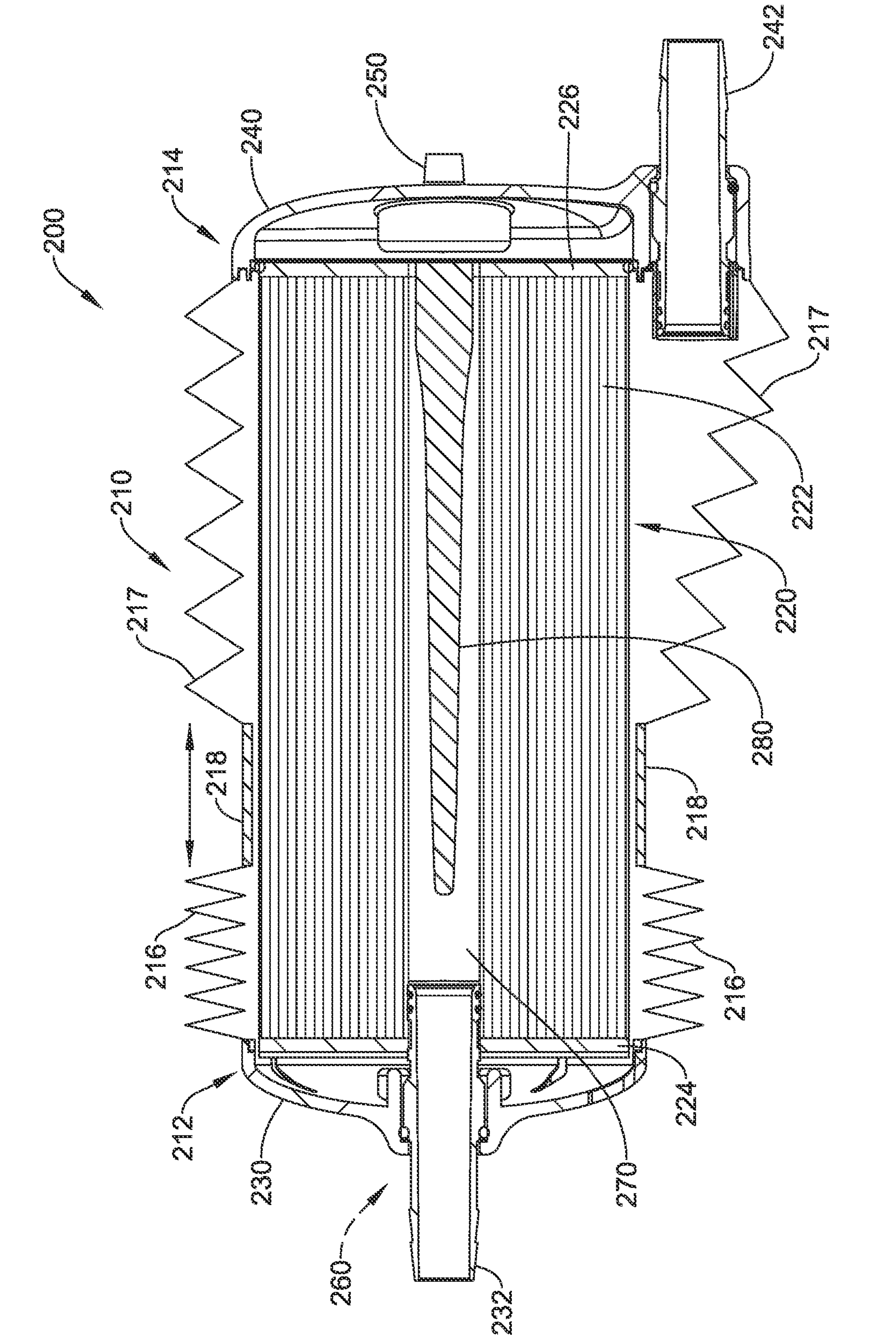
FIG. 8 illustrates an oxygenator including a housing having an axially movable portion.

FIG. 8 illustrates selected aspects of an oxygenator 200 for conditioning blood in extracorporeal circulation, such as with an extracorporeal life support (ECLS) system, for example. In some embodiments, an oxygenator 200 may comprise a housing 210 extending from a first end 212 to a second end 214 along a central longitudinal axis. In some embodiments, the housing 210 may be elongated in shape, with the central longitudinal axis extending from the first end 212 to the second end 214. In some embodiments, at least a portion of the housing 210 extending along the central longitudinal axis may be substantially cylindrical in shape.

The oxygenator 200 and/or the housing 210 may include a first cover or a first end cap 230 coupled to the first end 212 of the housing 210. In some embodiments, the first cover or the first end cap 230 may be fixedly attached to the housing 210. In some embodiments, the first cover or the first end cap 230 may be fixedly attached at the first end 212 of the housing 210. In some embodiments, the first cover or the first end cap 230 may be integrally and/or monolithically formed with the housing 210 as a single structure. In some alternative embodiments, the first cover or the first end cap 230 may be removable from the housing 210. Other configurations are also contemplated.

The oxygenator 200 and/or the housing 210 may include a second cover or a second end cap 240 coupled to the second end 214 of the housing 210. In some embodiments, the second cover or the second end cap 240 may be fixedly attached to the housing 210. In some embodiments, the second cover or the second end cap 240 may be fixedly attached at the second end 214 of the housing 210. In some embodiments, the second cover or the second end cap 240 may be integrally and/or monolithically formed with the housing 210 as a single structure. In some alternative embodiments, the second cover or the second end cap 240 may be removable from the housing 210. Other configurations are also contemplated.

In some embodiments, the housing 210 may have a fixed axial length. In some embodiments, the first cover or the first end cap 230 may be a fixed distance from the second cover or the second end cap 240.

In some embodiments, the housing 210 may comprise a first accordion portion 216, a second accordion portion 217, and a rigid tubular portion 218 disposed between and fixedly attached to the first accordion portion 216 and the second accordion portion 217. In some embodiments, the first accordion portion 216 and/or the second accordion portion 217 may be baffled, pleated, flexible, elastic, and/or may have other properties and/or configurations that permit the first accordion portion 216 and/or the second accordion portion 217 to resiliently shift, move, expand, and/or contract in an axial direction. A proximal end of the rigid tubular portion 218 may be fixedly attached to a distal end of the first accordion portion 216. A distal end of the rigid tubular portion 218 may be fixedly attached to a proximal end of the second accordion portion.

In some embodiments, the first accordion portion 216 may extend between the first end 212 of the housing 210 and the rigid tubular portion 218. In some embodiments, the first accordion portion 216 may extend from the first end 212 of the housing 210 to the rigid tubular portion 218. In some embodiments, the first accordion portion 216 may extend between the first cover or the first end cap 230 and the rigid tubular portion 218. In some embodiments, the first accordion portion 216 may extend from the first cover or the first end cap 230 to the rigid tubular portion 218.

In some embodiments, the second accordion portion 217 may extend between the rigid tubular portion 218 and the second end 214 of the housing 210. In some embodiments, the second accordion portion 217 may extend from the rigid tubular portion 218 to the second end 214 of the housing 210. In some embodiments, the second accordion portion 217 may extend between the rigid tubular portion 218 and the first cover or the first end cap 230. In some embodiments, the second accordion portion 217 may extend from the rigid tubular portion 218 to the first cover or the first end cap 230. In some embodiments, a distal end of the second accordion portion 217 may be disposed proximal of the second end 214 of the housing 210 and/or the first cover or the first end cap 230. In some embodiments, the distal end of the second accordion portion 217 may be axially spaced apart from the second end 214 of the housing 210 and/or the first cover or the first end cap 230. Other configurations are also contemplated.

The rigid tubular portion 218 of the housing 210 may be axially movable along the central longitudinal axis relative to the first cover or the first end cap 230 and/or the second cover or the second end cap 240. As the rigid tubular portion

218 of the housing 210 is moved axially along the central longitudinal axis, the first accordion portion 216 and/or the second accordion portion 217 may expand and/or contract axially. For example, as the rigid tubular portion 218 of the housing 210 is moved axially along the central longitudinal axis in a distal direction (e.g., toward the second cover or the second end cap 240), the first accordion portion 216 may expand axially and the second accordion portion 217 may contract axially. Similarly, as the rigid tubular portion 218 of the housing 210 is moved axially along the central longitudinal axis in a proximal direction (e.g., toward the first cover or the first end cap 230), the first accordion portion 216 may contract axially and the second accordion portion 217 may expand axially.

The oxygenator 200 may comprise a gas exchanger 220 disposed within the housing 210. In some embodiments, the gas exchanger 220 may be disposed between the first end 212 of the housing 210 and the second end 214 of the housing 210. In at least some embodiments, the gas exchanger 220 may include a bundle of hollow gas exchange fibers 222. In some embodiments, the bundle of hollow gas exchange fibers 222 may extend between the first end 212 of the housing 210 and the second end 214 of the housing 210. In some embodiments, the bundle of hollow gas exchange fibers 222 may extend from the first end 212 of the housing 210 to the second end 214 of the housing 210. In some embodiments, the bundle of hollow gas exchange fibers 222 may extend between the first cover or the first end cap 230 and the second cover or the second end cap 240. In some embodiments, the bundle of hollow gas exchange fibers 222 may extend from the first cover or the first end cap 230 to the second cover or the second end cap 240. Other configurations are also contemplated.

In some embodiments, the gas exchanger 220 may include a first potting body 224 disposed proximate the first end 212 of the housing 210 and a second potting body 226 disposed proximate the second end 214 of the housing 210. In some embodiments, the first potting body 224 may be fixedly attached to the first cover or the first end cap 230. In some embodiments, the second potting body 226 may be fixedly attached to the second cover or the second end cap 240. The bundle of hollow gas exchange fibers 222 may extend from the first potting body 224 to the second potting body 226. In some embodiments, the first potting body 224 and/or the second potting body 226 may be formed from resin or a polymeric material. In some embodiments, the first potting body 224 may be formed into and/or may be integrally or monolithically formed with the first cover or the first end cap 230. In some embodiments, the second potting body 226 may be formed into and/or may be integrally or monolithically formed with the second cover or the second end cap 240. Proximal and/or upstream ends of the bundle of hollow gas exchange fibers 222 may be fixedly attached to and/or may be embedded within the first potting body 224. Distal and/or downstream ends of the bundle of hollow gas exchange fibers 222 may be fixedly attached to and/or may be embedded within the second potting body 226. The gas exchanger 220 may be configured such that blood flow through the gas exchanger 220 may pass over and/or around the bundle of hollow gas exchange fibers 222 to facilitate gas exchange therebetween.

The first cover or the first end cap 230 and the second cover or the second end cap 240 may be disposed on opposite sides of the gas exchanger 220 and/or the bundle of hollow gas exchange fibers 222. The oxygenator 200, the housing 210, and/or the first cover or the first end cap 230 may include a blood inlet port 232 in fluid communication with the gas exchanger 220 and configured to connect to an extracorporeal life support system. The blood inlet port 232 may be configured to be in fluid communication with a patient's venous blood flow. In some embodiments, the blood inlet port 232 may be disposed and/or positioned upstream of the gas exchanger 220. In some embodiments, the blood inlet port 232 may be disposed proximate the first end 212 of the housing 210. In some embodiments, the housing 210 and/or the first cover or the first end cap 230 may include a purging line port through which air can be purged from the oxygenator 200 and/or the housing 210.

The oxygenator 200, the housing 210, and/or the second cover or the second end cap 240 may include a blood outlet port 242 in fluid communication with the gas exchanger 220 and configured to connect to the extracorporeal life support system. The blood outlet port 242 may be configured to be in fluid communication with a patient's arterial blood flow. In some embodiments, the blood outlet port 242 may be disposed and/or positioned downstream of the gas exchanger 220. In some embodiments, the blood outlet port 242 may be disposed proximate the second end 214 of the housing 210. In at least some embodiments, the blood outlet port 242 may be disposed on an opposite side of the gas exchanger 220 and/or the bundle of hollow gas exchange fibers 222 from the blood inlet port 232.

The oxygenator 200 and/or the housing 210 may include a gas inlet port 250 in fluid communication with the gas exchanger 220, the first potting body 224, and/or the bundle of hollow gas exchange fibers 222. In some embodiments, the gas inlet port 250 may be disposed in and/or adjacent to the second cover or the second end cap 240. In some embodiments, the gas inlet port 250 may be disposed at a position that is laterally and/or radially offset from the central longitudinal axis of the housing 210. In some embodiments, the gas inlet port 250 may be disposed at a position that is coaxial with the central longitudinal axis of the housing 210. Other configurations are also contemplated. The gas inlet port 250 may be configured to connect to a gas supply source via tubing (not shown) to transport gas (e.g., oxygen, air, etc.) to the oxygenator 200, the gas exchanger 220, and/or the bundle of hollow gas exchange fibers 222.

The oxygenator 200 and/or the housing 210 may include a gas outlet port 260 in fluid communication with the gas exchanger 220, the second potting body 226, and/or the bundle of hollow gas exchange fibers 222. In some embodiments, the gas outlet port 260 may be disposed in and/or adjacent to the first cover or the first end cap 230. It is noted that the gas outlet port 260 is not expressly visible in the figures. However, it is contemplated that the gas outlet port 260 may be similar in form, function, and/or location to the gas outlet port 160 described above. In some embodiments, the gas outlet port 260 may be disposed at a position that is laterally and/or radially offset from the central longitudinal axis of the housing 210. In some embodiments, the gas outlet port 260 may be disposed at a position that is coaxial with the central longitudinal axis of the housing 210. Other configurations are also contemplated. The gas outlet port 260 may be configured to transport gas (e.g., oxygen, carbon dioxide, air, etc.) away from the oxygenator 200. In some embodiments, the gas outlet port 260 may be in fluid communication with the atmosphere. In some alternative embodiments, the gas outlet port 260 may be configured to connect to a vacuum source, such as via tubing. In some embodiments, the oxygenator 200 and/or the housing 210 may be devoid of a dedicated gas outlet port in fluid communication with the gas exchanger 220, the second potting body 226, and/or the bundle of hollow gas exchange fibers 222. In some embodiments, the oxygenator 200 and/or the housing 210 may include one or more vent openings disposed in and/or adjacent to the first cover or the first end cap 230 and in fluid communication with the gas exchanger 220, the second potting body 226, and/or the bundle of hollow gas exchange fibers 222. In some embodiments, the oxygenator 200 and/or the housing 210 may include the gas outlet port 260 and the one or more vent openings disposed in and/or adjacent to the first cover or the first end cap 230. In some embodiments, the one or more vent openings may be vented to atmosphere. In some embodiments, the bundle of hollow gas exchange fibers 222 may be disposed within the housing 210. In some embodiments, the bundle of hollow gas exchange fibers 222 may extend between the first end 212 of the housing 210 and the second end 214 of the housing 210. In some embodiments, the bundle of hollow gas exchange fibers 222 may extend longitudinally between the first end 212 of the housing 210 and the second end 214 of the housing 210. In some embodiments, the bundle of hollow gas exchange fibers 222 may extend from the first end 212 of the housing 210 to the second end of the housing 210. As discussed herein, the bundle of hollow gas exchange fibers 222 may extend from the first potting body 224 to the second potting body 226.

The bundle of hollow gas exchange fibers 222 may be arranged in one or more configurations. In some embodiments, the bundle of hollow gas exchange fibers 222 may be arranged such that the bundle of hollow gas exchange fibers 222 is substantially parallel to each other and/or the central longitudinal axis of the housing 210. In some embodiments, the bundle of hollow gas exchange fibers 222 may be arranged such that the bundle of hollow gas exchange fibers 222 is wound around the central longitudinal axis of the housing 210. In some embodiments, the bundle of hollow gas exchange fibers 222 may be arranged such that the bundle of hollow gas exchange fibers 222 is wound helically around the central longitudinal axis of the housing 210. In some embodiments, the bundle of hollow gas exchange fibers 222 may be arranged in a plurality of layers, wherein fibers within each layer are oriented at an oblique angle to fibers within each immediately adjacent layer. In some embodiments, the bundle of hollow gas exchange fibers 222 may be arranged in a plurality of layers, wherein fibers within each layer are oriented substantially perpendicular to fibers within each immediately adjacent layer. Other configurations, including combinations thereof, are also contemplated.

In some embodiments, the oxygenator 200, the housing 210, and/or the gas exchanger 220 may include a blood lumen 270 disposed therein. The blood lumen 270 may be in fluid communication with the blood inlet port 232 and the blood outlet port 242. In at least some embodiments, the blood lumen 270 may be disposed and/or oriented coaxially with the blood inlet port 232. In at least some embodiments, the blood outlet port 242 may be disposed laterally and/or radially offset from the blood lumen 270. The blood lumen 270 may carry and/or direct blood flowing into the oxygenator 200 and/or the housing 210 into and/or through the gas exchanger 220.

In some embodiments, the oxygenator 200 and/or the gas exchanger 220 may include a diverter 280 disposed therein. In some embodiments, the diverter 280 may be disposed along and/or parallel to the central longitudinal axis of the housing 210. In some embodiments, the diverter 280 may be disposed in line with and/or coaxial with the blood inlet port 232. In some embodiments, the diverter 280 may be disposed within the blood lumen 270 and/or the gas exchanger 220. The diverter 280 may be configured to disrupt blood flow within the blood lumen 270 and/or to direct blood flowing into the gas exchanger 220 radially outward toward and/or into the bundle of hollow gas exchange fibers 222. In some embodiments, the diverter 280 may extend proximally from the second cover or the second end cap 240, and/or the second potting body 226. In some embodiments, the diverter 280 may be tapered radially inward in a proximal direction or an upstream direction and/or may be tapered radially outward in a distal direction or a downstream direction. Other configurations are also contemplated. The diverter 280 may be shaped, sized, and configured to limit damage to blood cells (e.g., lysing) as much as possible. In some embodiments, the diverter 280 may include channels, grooves, ridges, guides, blades, etc. formed in or extending from a generally conical outer surface.

During use, gas may be transferred between the gas exchanger 220 and/or the bundle of hollow gas exchange fibers 222 and blood flowing through the oxygenator 200 and/or the gas exchanger 220 (e.g., oxygen into the blood, carbon dioxide out of the blood, etc.).

In some embodiments, a blood conditioning system and/or the oxygenator 200 may include a pump (not shown) configured to drive fluid flow through the oxygenator 200. In some embodiments, the pump may be fluidly coupled to the oxygenator 200 via tubing. In some embodiments, the pump may extend from the housing 210 and/or the first cover or the first end cap 230 of the oxygenator 200. In some embodiments, the pump may be fixedly attached directly to the oxygenator 200, the housing 210, and/or the first cover or the first end cap 230. In some embodiments, the pump may be integrally formed with the housing 210 and/or the first cover or the first end cap 230 of the oxygenator 200. In some embodiments, the blood conditioning system and/or the oxygenator 200 may be devoid of tubing between and/or connecting the pump and the oxygenator 200. Other configurations are also contemplated.

In some embodiments, the blood conditioning system and/or the oxygenator 200 may include a heat exchanger (not shown) configured to exchange heat with the blood. In some embodiments, the oxygenator 200 and the heat exchanger may be disposed within a single, integrated housing. In some embodiments, the heat exchanger may be a standalone device fluidly coupled to the blood conditioning system and/or the oxygenator 200 via tubing. Other configurations are also contemplated.

In some embodiments, the blood conditioning system and/or the oxygenator 200 may include a gaseous micro-emboli (GME) removal device configured to remove gaseous micro-emboli from the blood. In some embodiments, the oxygenator 200 and the gaseous micro-emboli (GME) removal device may be disposed within a single, integrated housing. In some embodiments, the gaseous micro-emboli (GME) removal device may be a standalone device fluidly coupled to the blood conditioning system and/or the oxygenator 200 via tubing. Other configurations are also contemplated.

While not expressly illustrated, it is also contemplated that the oxygenator 200 may include a cardioplegia port and/or a recirculation port. In some embodiments, the cardioplegia port and/or the recirculation port may be formed in the housing 210. In some embodiments, the cardioplegia port and/or the recirculation port may be formed in and/or may be in fluid communication with the housing 210 and/or an interior thereof. Other configurations and/or features known in the art are also contemplated.

The gas exchanger 220 and/or the bundle of hollow gas exchange fibers 222 may be disposed within the housing 210. The gas exchanger 220 and/or the bundle of hollow gas exchange fibers 222 may extend between the first end 212 of the housing 210 and the second end 214 of the housing 210. In some embodiments, at least a portion of the housing 210 may be configured to selectively move and/or translate axially with respect to the gas exchanger 220, the bundle of hollow gas exchange fibers 222, the first cover or the first end cap 230, and/or the second cover or the second end cap 240. In some embodiments, the rigid tubular portion 218 may be configured to shift between a proximal position and a distal position. The housing 210 may be configured to change and/or disrupt blood flow within the oxygenator 200 and/or the gas exchanger 220 to promote mixing and/or to reduce stagnation, which may reduce or prevent thrombus formation. In some embodiments, movement and/or shifting of the housing 210 and/or the rigid tubular portion 218 axially with respect to the gas exchanger 220 and/or the bundle of hollow gas exchange fibers 222 may increase mixing of blood therein and/or reduce stagnation of blood therein.

In some embodiments, the housing 210 and/or the rigid tubular portion 218 may extend circumferentially around the gas exchanger 220 and/or the bundle of hollow gas exchange fibers 222. In some embodiments, the first accordion portion 216 and/or the second accordion portion 217 may extend circumferentially around the gas exchanger 220 and/or the bundle of hollow gas exchange fibers 222. In at least some embodiments, the housing 210 and/or the rigid tubular portion 218 may extend circumferentially completely around the gas exchanger 220 and/or the bundle of hollow gas exchange fibers 222. In some embodiments, the first accordion portion 216 and/or the second accordion portion 217 may extend circumferentially completely around the gas exchanger 220 and/or the bundle of hollow gas exchange fibers 222. In some embodiments, the housing 210 and/or the rigid tubular portion 218 may extend around an entire circumference of the gas exchanger 220 and/or the bundle of hollow gas exchange fibers 222. In some embodiments, the first accordion portion 216 and/or the second accordion portion 217 may extend around an entire circumference of the gas exchanger 220 and/or the bundle of hollow gas exchange fibers 222.

In some embodiments, the rigid tubular portion 218 may be manually movable and/or translatable axially along the central longitudinal axis and/or with respect to the gas exchanger 220, the bundle of hollow gas exchange fibers 222, the first cover or the first end cap 230, and/or the second cover or the second end cap 240. In some embodiments, the rigid tubular portion 218 may be manually movable and/or translatable between the proximal position and the distal position. In some embodiments, the rigid tubular portion 218 may be configured to oscillate back and forth along the central longitudinal axis. In some embodiments, the rigid tubular portion 218 may be configured to oscillate back and forth along the central longitudinal axis at a frequency no more than the patient's heart rate. In some embodiments, the rigid tubular portion 218 may be configured to oscillate between the proximal position and the distal position. In some embodiments, the rigid tubular portion 218 may be configured to oscillate between the proximal position and the distal position at a frequency no more than the patient's heart rate.

In some embodiments, the oxygenator 200 may include an actuation apparatus configured to selectively move and/or translate the rigid tubular portion 218 axially with respect to the gas exchanger 220, the bundle of hollow gas exchange fibers 222, the first cover or the first end cap 230, and/or the second cover or the second end cap 240. In some embodiments, the actuation apparatus may be configured to move and/or translate the rigid tubular portion 218 between the proximal position and the distal position. In some embodiments, the actuation apparatus may be configured to operate in a cyclical manner. In some embodiments, the actuation apparatus may be configured to operate in a variable manner. In some embodiments, the actuation apparatus may be configured to oscillate the rigid tubular portion 218 axially back and forth along the central longitudinal axis. In some embodiments, the actuation apparatus may be configured to oscillate the rigid tubular portion 218 axially back and forth along the central longitudinal axis at a frequency no more than the patient's heart rate. In some embodiments, the actuation apparatus may be configured to oscillate the rigid tubular portion 218 axially between the proximal position and the distal position. In some embodiments, the actuation apparatus may be configured to oscillate the rigid tubular portion 218 axially between the proximal position and the distal position at a frequency no more than the patient's heart rate. Other configurations are also contemplated.

Various configurations and/or types of actuation apparatuses are contemplated in conjunction with the disclosure. In some embodiments, the actuation apparatus may include a shape memory material configured to move and/or translate the rigid tubular portion 218 between the proximal position and the distal position via changes in ambient temperature or another stimulus. In some embodiments, the actuation apparatus may include an electrically sensitive material configured to move and/or translate between the rigid tubular portion 218 between the proximal position and the distal position via changes in an applied electrical current and/or electrical resistance. In some embodiments, the actuation apparatus may be magnetically driven and/or may be configured to move and/or shift the rigid tubular portion 218 between the proximal position and the distal position in response to an applied magnetic field. In some embodiments, the actuation apparatus may include a mechanical structure configured to move and/or translate the rigid tubular portion 218 between the proximal position and the distal position. In some embodiments, the mechanical structure may be motor driven. Other configurations are also contemplated. In some embodiments, the actuation apparatus may include an expandable structure configured to move and/or translate the rigid tubular portion 218 between the proximal position and the distal position. In some embodiments, the expandable structure may be configured to move and/or translate the rigid tubular portion 218 between the proximal position and the distal position via changes in fluid pressure and/or volume therein. Other configurations are also contemplated.

FIG. 9 illustrates selected aspects of an oxygenator 300 for conditioning blood in extracorporeal circulation, such as with an extracorporeal life support (ECLS) system, for example. In some embodiments, an oxygenator 300 may comprise a housing 310 extending from a first end 312 to a second end 314 along a central longitudinal axis. In some embodiments, the housing 310 may be constructed from a substantially rigid material. In some embodiments, the housing 310 may be elongated in shape, with the central longitudinal axis extending from the first end 312 to the second end 314. In some embodiments, at least a portion of the housing 310 extending along the central longitudinal axis may be substantially cylindrical in shape.

The oxygenator 300 and/or the housing 310 may include a first cover or a first end cap 330 coupled to the first end 312 of the housing 310. In some embodiments, the first cover or the first end cap 330 may be fixedly attached to the housing 310. In some embodiments, the first cover or the first end cap 330 may be fixedly attached at the first end 312 of the housing 310. In some embodiments, the first cover or the first end cap 330 may be integrally and/or monolithically formed with the housing 310 as a single structure. In some alternative embodiments, the first cover or the first end cap 330 may be removable from the housing 310. Other configurations are also contemplated.

The oxygenator 300 and/or the housing 310 may include a second cover or a second end cap 340 coupled to the second end 314 of the housing 310. In some embodiments, the second cover or the second end cap 340 may be fixedly attached to the housing 310. In some embodiments, the second cover or the second end cap 340 may be fixedly attached at the second end 314 of the housing 310. In some embodiments, the second cover or the second end cap 340 may be integrally and/or monolithically formed with the housing 310 as a single structure. In some alternative embodiments, the second cover or the second end cap 340 may be removable from the housing 310. Other configurations are also contemplated.

In some embodiments, the housing 310 may have a fixed axial length. In some embodiments, the first cover or the first end cap 330 may be a fixed distance from the second cover or the second end cap 340.

The oxygenator 300 may comprise a gas exchanger 320 disposed within the housing 310. In some embodiments, the gas exchanger 320 may be disposed between the first end 312 of the housing 310 and the second end 314 of the housing 310. In at least some embodiments, the gas exchanger 320 may include a bundle of hollow gas exchange fibers 322. In some embodiments, the bundle of hollow gas exchange fibers 322 may extend between the first end 312 of the housing 310 and the second end 314 of the housing 310. In some embodiments, the bundle of hollow gas exchange fibers 322 may extend between the first cover or the first end cap 330 and the second cover or the second end cap 340. Other configurations are also contemplated.

In some embodiments, the gas exchanger 320 may include a first potting body 324 disposed proximate the first end 312 of the housing 310 and a second potting body 326 disposed proximate the second end 314 of the housing 310. The bundle of hollow gas exchange fibers 322 may extend from the first potting body 324 to the second potting body 326. In some embodiments, the first potting body 324 and/or the second potting body 326 may be formed from resin or a polymeric material. Proximal and/or upstream ends of the bundle of hollow gas exchange fibers 322 may be fixedly attached to and/or may be embedded within the first potting body 324. Distal and/or downstream ends of the bundle of hollow gas exchange fibers 322 may be fixedly attached to and/or may be embedded within the second potting body 326. The gas exchanger 320 may be configured such that blood flow through the gas exchanger 320 may pass over and/or around the bundle of hollow gas exchange fibers 322 to facilitate gas exchange therebetween.

The first cover or the first end cap 330 and the second cover or the second end cap 340 may be disposed on opposite sides of the gas exchanger 320 and/or the bundle of hollow gas exchange fibers 322. The oxygenator 300, the housing 310, and/or the first cover or the first end cap 330 may include a blood inlet port 332 in fluid communication with the gas exchanger 320 and configured to connect to an extracorporeal life support system. The blood inlet port 332 may be configured to be in fluid communication with a patient's venous blood flow. In some embodiments, the blood inlet port 332 may be disposed and/or positioned upstream of the gas exchanger 320. In some embodiments, the blood inlet port 332 may be disposed proximate the first end 312 of the housing 310. In some embodiments, the housing 310 and/or the first cover or the first end cap 330 may include a purging line port through which air can be purged from the oxygenator 300 and/or the housing 310.

The oxygenator 300, the housing 310, and/or the second cover or the second end cap 340 may include a blood outlet port 342 in fluid communication with the gas exchanger 320 and configured to connect to the extracorporeal life support system. The blood outlet port 342 may be configured to be in fluid communication with a patient's arterial blood flow. In some embodiments, the blood outlet port 342 may be disposed and/or positioned downstream of the gas exchanger 320. In some embodiments, the blood outlet port 342 may be disposed proximate the second end 314 of the housing 310. In at least some embodiments, the blood outlet port 342 may be disposed on an opposite side of the gas exchanger 320 and/or the bundle of hollow gas exchange fibers 322 from the blood inlet port 332.

The oxygenator 300 and/or the housing 310 may include a gas inlet port 350 in fluid communication with the gas exchanger 320, the first potting body 324, and/or the bundle of hollow gas exchange fibers 322. In some embodiments, the gas inlet port 350 may be disposed in and/or adjacent to the second cover or the second end cap 340. In some embodiments, the gas inlet port 350 may be disposed at a position that is laterally and/or radially offset from the central longitudinal axis of the housing 310. In some embodiments, the gas inlet port 350 may be disposed at a position that is coaxial with the central longitudinal axis of the housing 310. Other configurations are also contemplated. The gas inlet port 350 may be configured to connect to a gas supply source via tubing (not shown) to transport gas (e.g., oxygen, air, etc.) to the oxygenator 300, the gas exchanger 320, and/or the bundle of hollow gas exchange fibers 322.

The oxygenator 300 and/or the housing 310 may include a gas outlet port 260 in fluid communication with the gas exchanger 320, the second potting body 326, and/or the bundle of hollow gas exchange fibers 322. In some embodiments, the gas outlet port 360 may be disposed in and/or adjacent to the first cover or the first end cap 330. It is noted that the gas outlet port 360 is not expressly visible in the figures. However, it is contemplated that the gas outlet port 360 may be similar in form, function, and/or location to the gas outlet port 160 described above. In some embodiments, the gas outlet port 360 may be disposed at a position that is laterally and/or radially offset from the central longitudinal axis of the housing 310. In some embodiments, the gas outlet port 360 may be disposed at a position that is coaxial with the central longitudinal axis of the housing 310. Other configurations are also contemplated. The gas outlet port 360 may be configured to transport gas (e.g., oxygen, carbon dioxide, air, etc.) away from the oxygenator 300. In some embodiments, the gas outlet port 360 may be in fluid communication with the atmosphere. In some alternative embodiments, the gas outlet port 360 may be configured to connect to a vacuum source, such as via tubing. In some embodiments, the oxygenator 300 and/or the housing 310 may be devoid of a dedicated gas outlet port in fluid communication with the gas exchanger 320, the second potting body 326, and/or the bundle of hollow gas exchange fibers 322. In some embodiments, the oxygenator 300 and/or the housing 310 may include one or more vent openings disposed in and/or adjacent to the first cover or the first end cap 330 and in fluid communication with the gas exchanger 320, the second potting body 326, and/or the bundle of hollow gas exchange fibers 322. In some embodiments, the oxygenator 300 and/or the housing 310 may include the gas outlet port 360 and the one or more vent openings disposed in and/or adjacent to the first cover or the first end cap 330. In some embodiments, the one or more vent openings may be vented to atmosphere.

In some embodiments, the bundle of hollow gas exchange fibers 322 may be disposed within the housing 310. In some embodiments, the bundle of hollow gas exchange fibers 322 may extend between the first end 312 of the housing 310 and the second end 314 of the housing 310. In some embodiments, the bundle of hollow gas exchange fibers 322 may extend longitudinally between the first end 312 of the housing 310 and the second end 314 of the housing 310. As discussed herein, the bundle of hollow gas exchange fibers 322 may extend from the first potting body 324 to the second potting body 326.

The bundle of hollow gas exchange fibers 322 may be arranged in one or more configurations. In some embodiments, the bundle of hollow gas exchange fibers 322 may be arranged such that the bundle of hollow gas exchange fibers 322 is substantially parallel to each other and/or the central longitudinal axis of the housing 310. In some embodiments, the bundle of hollow gas exchange fibers 322 may be arranged such that the bundle of hollow gas exchange fibers 322 is wound around the central longitudinal axis of the housing 310. In some embodiments, the bundle of hollow gas exchange fibers 322 may be arranged such that the bundle of hollow gas exchange fibers 322 is wound helically around the central longitudinal axis of the housing 310. In some embodiments, the bundle of hollow gas exchange fibers 322 may be arranged in a plurality of layers, wherein fibers within each layer are oriented at an oblique angle to fibers within each immediately adjacent layer. In some embodiments, the bundle of hollow gas exchange fibers 322 may be arranged in a plurality of layers, wherein fibers within each layer are oriented substantially perpendicular to fibers within each immediately adjacent layer. Other configurations, including combinations thereof, are also contemplated.

In some embodiments, the oxygenator 300, the housing 310, and/or the gas exchanger 320 may include a blood lumen 370 disposed therein. The blood lumen 370 may be in fluid communication with the blood inlet port 332 and the blood outlet port 342. In at least some embodiments, the blood lumen 370 may be disposed and/or oriented coaxially with the blood inlet port 332. In at least some embodiments, the blood outlet port 342 may be disposed laterally and/or radially offset from the blood lumen 370. The blood lumen 370 may carry and/or direct blood flowing into the oxygenator 300 and/or the housing 310 into and/or through the gas exchanger 320.

In some embodiments, the oxygenator 300 and/or the gas exchanger 320 may include a diverter 380 disposed therein. In some embodiments, the diverter 380 may be disposed along and/or parallel to the central longitudinal axis of the housing 310. In some embodiments, the diverter 380 may be disposed in line with and/or coaxial with the blood inlet port 332. In some embodiments, the diverter 380 may be disposed within the blood lumen 370 and/or the gas exchanger 320. The diverter 380 may be configured to disrupt blood flow within the blood lumen 370 and/or to direct blood flowing into the gas exchanger 320 radially outward toward and/or into the bundle of hollow gas exchange fibers 322. In some embodiments, the diverter 380 may extend proximally from the second potting body 326. In some embodiments, the diverter 380 may be tapered radially inward in a proximal direction or an upstream direction and/or may be tapered radially outward in a distal direction or a downstream direction. Other configurations are also contemplated. The diverter 380 may be shaped, sized, and configured to limit damage to blood cells (e.g., lysing) as much as possible. In some embodiments, the diverter 380 may include channels, grooves, ridges, guides, blades, etc. formed in or extending from a generally conical outer surface.

During use, gas may be transferred between the gas exchanger 320 and/or the bundle of hollow gas exchange fibers 322 and blood flowing through the oxygenator 300 and/or the gas exchanger 320 (e.g., oxygen into the blood, carbon dioxide out of the blood, etc.).

In some embodiments, a blood conditioning system and/or the oxygenator 300 may include a pump (not shown) configured to drive fluid flow through the oxygenator 300. In some embodiments, the pump may be fluidly coupled to the oxygenator 300 via tubing. In some embodiments, the pump may extend from the housing 310 and/or the first cover or the first end cap 330 of the oxygenator 300. In some embodiments, the pump may be fixedly attached directly to the oxygenator 300, the housing 310, and/or the first cover or the first end cap 330. In some embodiments, the pump may be integrally formed with the housing 310 and/or the first cover or the first end cap 330 of the oxygenator 300. In some embodiments, the blood conditioning system and/or the oxygenator 300 may be devoid of tubing between and/or connecting the pump and the oxygenator 300. Other configurations are also contemplated.

In some embodiments, the blood conditioning system and/or the oxygenator 300 may include a heat exchanger (not shown) configured to exchange heat with the blood. In some embodiments, the oxygenator 300 and the heat exchanger may be disposed within a single, integrated housing. In some embodiments, the heat exchanger may be a standalone device fluidly coupled to the blood conditioning system and/or the oxygenator 300 via tubing. Other configurations are also contemplated.

In some embodiments, the blood conditioning system and/or the oxygenator 300 may include a gaseous micro-emboli (GME) removal device configured to remove gaseous micro-emboli from the blood. In some embodiments, the oxygenator 300 and the gaseous micro-emboli (GME) removal device may be disposed within a single, integrated housing. In some embodiments, the gaseous micro-emboli (GME) removal device may be a standalone device fluidly coupled to the blood conditioning system and/or the oxygenator 300 via tubing. Other configurations are also contemplated.

While not expressly illustrated, it is also contemplated that the oxygenator 300 may include a cardioplegia port and/or a recirculation port. In some embodiments, the cardioplegia port and/or the recirculation port may be formed in the housing 310. In some embodiments, the cardioplegia port and/or the recirculation port may be formed in and/or may be in fluid communication with the housing 310 and/or an interior thereof. Other configurations and/or features known in the art are also contemplated.

The gas exchanger 320 and/or the bundle of hollow gas exchange fibers 322 may be disposed within the housing 310. The gas exchanger 320 and/or the bundle of hollow gas exchange fibers 322 may extend between the first end 312 of the housing 310 and the second end 314 of the housing 310. In some embodiments, the gas exchanger 320 and/or the bundle of hollow gas exchange fibers 322 may be axially movable and/or translatable relative to the housing 310 along the central longitudinal axis. In some embodiments, the gas exchanger 320 and/or the bundle of hollow gas exchange fibers 322 may be configured to selectively move and/or translate axially with respect to the housing 310, the first cover or the first end cap 330, and/or the second cover or the second end cap 340. In some embodiments, the gas exchanger 320 and/or the bundle of hollow gas exchange fibers 322 may be configured to shift between a proximal position and a distal position. Movement and/or translation of the gas exchanger 320 and/or the bundle of hollow gas exchange fibers 322 within and/or relative to the housing 310, the first cover or the first end cap 330, and/or the second cover or the second end cap 340 may be configured to change and/or disrupt blood flow within the oxygenator 300 and/or the gas exchanger 320 to promote mixing and/or to reduce stagnation, which may reduce or prevent thrombus formation. In some embodiments, movement and/or shifting of the gas exchanger 320 and/or the bundle of hollow gas exchange fibers 322 axially with respect to the housing 310, the first cover or the first end cap 330, and/or the second cover or the second end cap 340 may increase mixing of blood therein and/or reduce stagnation of blood therein.

In some embodiments, the housing 310 may extend circumferentially around the gas exchanger 320 and/or the bundle of hollow gas exchange fibers 322. In at least some embodiments, the housing 310 may extend circumferentially completely around the gas exchanger 320 and/or the bundle of hollow gas exchange fibers 322. In some embodiments, the housing 210 may extend around an entire circumference of the gas exchanger 320 and/or the bundle of hollow gas exchange fibers 322.

In some embodiments, the gas exchanger 320 and/or the bundle of hollow gas exchange fibers 322 may be manually movable and/or translatable axially along the central longitudinal axis and/or with respect to the housing 310, the first cover or the first end cap 330, and/or the second cover or the second end cap 340. In some embodiments, the gas exchanger 320 and/or the bundle of hollow gas exchange fibers 322 may be manually movable and/or translatable between the proximal position and the distal position. In some embodiments, the gas exchanger 320 and/or the bundle of hollow gas exchange fibers 322 may be configured to oscillate back and forth along the central longitudinal axis. In some embodiments, the gas exchanger 320 and/or the bundle of hollow gas exchange fibers 322 may be configured to oscillate back and forth along the central longitudinal axis at a frequency no more than the patient's heart rate. In some embodiments, the gas exchanger 320 and/or the bundle of hollow gas exchange fibers 322 may be configured to oscillate between the proximal position and the distal position. In some embodiments, the gas exchanger 320 and/or the bundle of hollow gas exchange fibers 322 may be configured to oscillate between the proximal position and the distal position at a frequency no more than the patient's heart rate.

In some embodiments, the oxygenator 300 may include an actuation apparatus configured to selectively move and/or translate the gas exchanger 320 and/or the bundle of hollow gas exchange fibers 322 axially with respect to the housing 310, the first cover or the first end cap 330, and/or the second cover or the second end cap 340. In some embodiments, the actuation apparatus may be configured to move and/or translate the gas exchanger 320 and/or the bundle of hollow gas exchange fibers 322 between the proximal position and the distal position. In some embodiments, the actuation apparatus may be configured to operate in a cyclical manner. In some embodiments, the actuation apparatus may be configured to operate in a variable manner. In some embodiments, the actuation apparatus may be configured to oscillate the gas exchanger 320 and/or the bundle of hollow gas exchange fibers 322 axially back and forth along the central longitudinal axis. In some embodiments, the actuation apparatus may be configured to oscillate the gas exchanger 320 and/or the bundle of hollow gas exchange fibers 322 axially back and forth along the central longitudinal axis at a frequency no more than the patient's heart rate. In some embodiments, the actuation apparatus may be configured to oscillate the gas exchanger 320 and/or the bundle of hollow gas exchange fibers 322 axially between the proximal position and the distal position. In some embodiments, the actuation apparatus may be configured to oscillate the gas exchanger 320 and/or the bundle of hollow gas exchange fibers 322 axially between the proximal position and the distal position at a frequency no more than the patient's heart rate. Other configurations are also contemplated.

Various configurations and/or types of actuation apparatuses are contemplated in conjunction with the disclosure. In some embodiments, the actuation apparatus may include a shape memory material configured to move and/or translate the gas exchanger 320 and/or the bundle of hollow gas exchange fibers 322 between the proximal position and the distal position via changes in ambient temperature or another stimulus. In some embodiments, the actuation apparatus may include an electrically sensitive material configured to move and/or translate between the gas exchanger 320 and/or the bundle of hollow gas exchange fibers 322 between the proximal position and the distal position via changes in an applied electrical current and/or electrical resistance. In some embodiments, the actuation apparatus may include a mechanical structure configured to move and/or translate the gas exchanger 320 and/or the bundle of hollow gas exchange fibers 322 between the proximal position and the distal position. In some embodiments, the mechanical structure may be motor driven. Other configurations are also contemplated. In some embodiments, the actuation apparatus may include an expandable structure configured to move and/or translate the gas exchanger 320 and/or the bundle of hollow gas exchange fibers 322 between the proximal position and the distal position. In some embodiments, the expandable structure may be configured to move and/or translate the gas exchanger 320 and/or the bundle of hollow gas exchange fibers 322 between the proximal position and the distal position via changes in fluid pressure and/or volume therein. Other configurations are also contemplated.

The oxygenator 300 and/or the gas exchanger 320 may comprise a first accordion portion 316 fixedly attached to the first cover or the first end cap 330 and defining a first accordion chamber 317 between the first potting body 324 and/or the bundle of hollow gas exchange fibers 322 and the first cover or the first end cap 330. The first potting body 324 may be fixedly attached to a distal end of the first accordion portion 316. The first accordion chamber 317 may be in fluid communication with the gas outlet port 360 and may be configured to carry gas away from the first potting body 324 and/or the bundle of hollow gas exchange fibers 322.

The oxygenator 300 and/or the gas exchanger 320 may comprise a second accordion portion 318 fixedly attached to the second cover or the second end cap 340 and defining a second accordion chamber 319 between the second potting body 326 and/or the bundle of hollow gas exchange fibers 322 and the second cover or the second end cap 340. The second potting body 326 may be fixedly attached to a proximal end of the second accordion portion 318. The second accordion chamber 319 may be in fluid communication with the gas inlet port 350 and may be configured to carry gas toward and/or to the second potting body 326 and/or the bundle of hollow gas exchange fibers 322. The second accordion portion 318 and/or the second accordion chamber 319 may be axially spaced apart from the first accordion portion 316 and/or the first accordion chamber 317. In at least some embodiments, the bundle of hollow gas exchange fibers 322 may be disposed axially between the first accordion portion 316 and/or the first accordion chamber 317 and the second accordion portion 318 and/or the second accordion chamber 319. In some embodiments, the first accordion portion 316 and/or the second accordion portion 318 may be baffled, pleated, flexible, elastic, and/or may have other properties and/or configurations that permit the first accordion portion 316 and/or the second accordion portion 318 to resiliently shift, move, expand, and/or contract in an axial direction.

The gas exchanger 320 and/or the bundle of hollow gas exchange fibers 322 may be axially movable along the central longitudinal axis relative to the first cover or the first end cap 230 and/or the second cover or the second end cap 240. As the gas exchanger 320 and/or the bundle of hollow gas exchange fibers 322 is moved axially along the central longitudinal axis, the first accordion portion 316 and/or the second accordion portion 318 may expand and/or contract axially. For example, as the gas exchanger 320 and/or the bundle of hollow gas exchange fibers 322 is moved axially along the central longitudinal axis in a distal direction (e.g., toward the second cover or the second end cap 240), the first accordion portion 316 may expand axially and the second accordion portion 318 may contract axially. Similarly, as the gas exchanger 320 and/or the bundle of hollow gas exchange fibers 322 is moved axially along the central longitudinal axis in a proximal direction (e.g., toward the first cover or the first end cap 230), the first accordion portion 316 may contract axially and the second accordion portion 318 may expand axially.

The materials that can be used for the various components of the oxygenator and the various elements thereof disclosed herein may include those commonly associated with medical devices. For simplicity purposes, the following discussion refers to the device. However, this is not intended to limit the devices, components, and methods described herein, as the discussion may be applied to other elements, members, components, or devices disclosed herein, such as, but not limited to, the housing, the second cover, the first cover, the diverter, the gas exchanger, the bundle of hollow gas exchange fibers, etc. and/or elements or components thereof.

In some embodiments, the device and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, ether or ester based copolymers (for example, butylene/poly (alkylene ether) phthalate and/or other polyester elastomers), polyamide, elastomeric polyamides, block polyamide/ethers, polyether block amide (PEBA, for example PEBAX®), ethylene vinyl acetate copolymers (EVA), silicones, polyethylene (PE), high-density polyethylene, low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide, polysulfone, nylon, nylon-12, perfluoro (propyl vinyl ether) (PFA), ethylene vinyl alcohol, polyolefin, polystyrene, epoxy, polyvinylidene chloride (PVdC), poly(styrene-b-isobutylene-b-styrene), polycarbonates, polyisobutylene (PIB), polyisobutylene polyurethane (PIBU), polymethylpentene (PMP), polyurethane silicone copolymers, ionomers, biocompatible polymers, other suitable materials, or mixtures, combinations, copolymers thereof, polymer/metal composites, and the like.

Some examples of suitable metals and metal alloys include stainless steel, such as 304 or 316 stainless steel or variations thereof; mild steel; nickel-titanium alloy such as linear clastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; or any other suitable material.

In some embodiments, the device and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryroyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. An oxygenator, comprising:
- a housing extending from a first end to a second end along a central longitudinal axis;
- a first end cap fixedly attached to the first end of the housing;
- a second end cap fixedly attached to the second end of the housing; and
- a bundle of hollow gas exchange fibers extending between the first end of the housing and the second end of the housing;
- wherein the first end cap and the second end cap are each rotatable about the central longitudinal axis;
- wherein rotating the first end cap in a first direction and rotating the second end cap in a second direction opposite the first direction causes the housing to shorten.

2. The oxygenator of claim 1, wherein the housing includes a flexible portion disposed between the first end and the second end.

3. The oxygenator of claim 1, wherein the housing extends continuously from the first end of the housing to the second end of the housing.

4. The oxygenator of claim 3, wherein the bundle of hollow gas exchange fibers comprises:
- a first bundle of hollow gas exchange fibers extending between the first end of the housing and a middle junction disposed between the first end of the housing and the second end of the housing; and
- a second bundle of hollow gas exchange fibers extending between the middle junction and the second end of the housing;
- wherein the second end cap is rotatable simultaneously with the first end cap.

5. The oxygenator of claim 4, wherein the first bundle of hollow gas exchange fibers and the second bundle of hollow gas exchange fibers are each fixedly attached to the middle junction.

6. The oxygenator of claim 1, wherein the bundle of hollow gas exchange fibers comprises:
- a first bundle of hollow gas exchange fibers extending between the first end of the housing and a middle junction disposed between the first end of the housing and the second end of the housing; and
- a second bundle of hollow gas exchange fibers extending between the middle junction and the second end of the housing;
- wherein the first end cap and the second end cap are each configured to oscillate between the first direction and the second direction.

7. The oxygenator of claim 1, wherein the housing includes a first housing portion fixedly attached to the first end cap and a second housing portion fixedly attached to the second end cap, wherein the first housing portion is axially spaced apart from the second housing portion.

8. The oxygenator of claim 7, wherein the first housing portion is rotatable relative to the second housing portion.

9. The oxygenator of claim 7, wherein the first housing portion is coupled to the second housing portion by a bridge section.

10. The oxygenator of claim 9, wherein the first housing portion is rotatable relative to the bridge section and the second housing portion is rotatable relative to the bridge section.

11. The oxygenator of claim 7, wherein the first housing portion comprises a first bundle of hollow gas exchange fibers and the second housing portion comprises a second bundle of hollow gas exchange fibers.

12. An oxygenator, comprising:
- a housing extending from a first end to a second end along a central longitudinal axis;
- a first end cap fixedly attached to the first end of the housing;
- a second end cap fixedly attached to the second end of the housing;
- a first bundle of hollow gas exchange fibers extending between the first end of the housing and a middle junction disposed between the first end of the housing and the second end of the housing; and
- a second bundle of hollow gas exchange fibers extending between the middle junction and the second end of the housing;
- wherein the first end cap and the second end cap are each rotatable about the central longitudinal axis;
- wherein rotating the first end cap in a first direction and rotating the second end cap in a second direction opposite the first direction causes the housing to shorten.

13. The oxygenator of claim 12, wherein rotation of the first end cap about the central longitudinal axis moves the first end cap toward or away from the middle junction.

14. The oxygenator of claim 13, wherein rotation of the second end cap about the central longitudinal axis moves the second end cap toward or away from the middle junction.

15. The oxygenator of claim 12, wherein the first end cap and the second end cap are each configured to oscillate relative to the middle junction.

16. The oxygenator of claim 12, wherein the housing includes a first housing portion fixedly attached to the first end cap and a second housing portion fixedly attached to the second end cap, wherein the first housing portion is axially spaced apart from the second housing portion.

17. The oxygenator of claim 16, wherein the first housing portion is rotatable relative to the second housing portion.

18. The oxygenator of claim 16, wherein the first housing portion is coupled to the second housing portion by a bridge section.

* * * * *